United States Patent
Buczkowski et al.

(10) Patent No.: US 9,846,122 B2
(45) Date of Patent: *Dec. 19, 2017

(54) OPTICAL METROLOGY SYSTEM FOR SPECTRAL IMAGING OF A SAMPLE

(71) Applicant: Nanometrics Incorporated, Milpitas, CA (US)

(72) Inventors: Andrzej Buczkowski, Bend, OR (US); Mikhail Sluch, Redmond, OR (US)

(73) Assignee: Nanometrics Incorporated, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/178,484

(22) Filed: Jun. 9, 2016

(65) Prior Publication Data

US 2016/0290927 A1 Oct. 6, 2016

Related U.S. Application Data

(63) Continuation-in-part of application No. 14/936,635, filed on Nov. 9, 2015, now abandoned, which is a
(Continued)

(51) Int. Cl.
*G01N 21/00* (2006.01)
*G01N 21/64* (2006.01)
(Continued)

(52) U.S. Cl.
CPC ........ *G01N 21/6489* (2013.01); *G01J 3/2823* (2013.01); *G01N 21/47* (2013.01);
(Continued)

(58) Field of Classification Search
CPC ... H01J 37/32935; G01N 21/64; G01N 21/65; G01N 21/68; G01N 2105/1037; G01J 3/02

See application file for complete search history.

(56) References Cited

U.S. PATENT DOCUMENTS 6,587,193 B1 7/2003 Reinhron et al.
7,098,052 B2 8/2006 Higgs
(Continued)

FOREIGN PATENT DOCUMENTS

EP 1672355 A2 6/2006
JP S6453138 A 3/1989
(Continued)

OTHER PUBLICATIONS

Moore, C.J.L et al. (Jun. 2, 1990). "A spatially resolved spectrally resolved photoluminescence mapping system," *Journal of Crystal Growth*, Elsevier: Amsterdam, NL, vol. 103(1-4):21-27.
(Continued)

*Primary Examiner* — Abdullahi Nur
(74) *Attorney, Agent, or Firm* — Silicon Valley Patent Group LLP

(57) ABSTRACT

An optical metrology device is capable of detection of any combination of photoluminescence light, specular reflection of broadband light, and scattered light from a line across the width of a sample. The metrology device includes a first light source that produces a first illumination line on the sample. A scanning system may be used to scan an illumination spot across the sample to form the illumination line. A detector collects the photoluminescence light emitted along the illumination line. Additionally, a broadband illumination source may be used to produce a second illumination line on the sample, where the detector collects the broadband illumination reflected along the second illumination line. A signal collecting optic may collect the photoluminescence light and broadband light and focus it into a line, which is received by an optical conduit. The output end of the optical conduit has a shape that matches the entrance of the detector.

28 Claims, 13 Drawing Sheets

Related U.S. Application Data continuation of application No. 14/091,199, filed on Nov. 26, 2013, now Pat. No. 9,182,351.

(60) Provisional application No. 62/253,092, filed on Nov. 9, 2015.

(51) Int. Cl.
| | |
|---|---|
| *G01J 3/28* | (2006.01) |
| *G01N 21/47* | (2006.01) |
| *G01N 21/55* | (2014.01) |
| *G01N 21/88* | (2006.01) |
| *G01N 21/95* | (2006.01) |
| G01B 11/06 | (2006.01) |
| H04N 3/14 | (2006.01) |

(52) U.S. Cl.
CPC ......... *G01N 21/55* (2013.01); *G01N 21/6456* (2013.01); *G01N 21/88* (2013.01); *G01N 21/9501* (2013.01); *G01B 11/0625* (2013.01); *G01N 2021/4735* (2013.01); *G01N 2021/646* (2013.01); *G01N 2021/8822* (2013.01); *G01N 2021/8825* (2013.01); *G01N 2201/0638* (2013.01); *G01N 2201/06113* (2013.01); *G01N 2201/1053* (2013.01); *H04N 3/155* (2013.01)

(56) References Cited

U.S. PATENT DOCUMENTS

| | | | |
|---|---|---|---|
| 7,113,276 | B1 | 9/2006 | Higgs et al. |
| 7,149,366 | B1 | 12/2006 | Sun |
| 7,307,705 | B2 | 12/2007 | Treado |
| 7,532,326 | B2 | 5/2009 | Corcoran |
| 8,330,946 | B2 | 12/2012 | Buczkowski et al. |
| 9,182,351 | B2 * | 11/2015 | Buczkowski ...... G01N 21/6489 |
| 2006/0007439 | A1 | 1/2006 | Corcoran |
| 2007/0008525 | A1 | 1/2007 | Tuschel et al. |
| 2009/0135418 | A1 | 5/2009 | Wolff |
| 2010/0220316 | A1 | 9/2010 | Finarov |
| 2011/0169944 | A1 | 7/2011 | Zhao et al. |
| 2012/0292726 | A1 | 11/2012 | Wallace |
| 2013/0048873 | A1 | 2/2013 | Young et al. |

FOREIGN PATENT DOCUMENTS

| | | |
|---|---|---|
| WO | WO 2011/079354 A1 | 7/2011 |
| WO | WO 2013/023241 A1 | 2/2013 |

OTHER PUBLICATIONS

Invitation to Pay Additional Fees dated Jan. 23, 2015 for International Application No. PCT/US2014/062980 filed on Oct. 29, 2014 by Nanometrics Incorporated, 7 pages.

International Search Report and Written Opinion dated Apr. 29, 2015 for International Application No. PCT/US2014/062980 filed on Oct. 29, 2014 by Nanometrics Incorporated, 19 pages.

Semilab Semiconductor Physics Laboratory Co., Ltd. (Jun. 25, 2012). "Advanced in-line characterization and sorting of crystalline silicon photovoltaic wafers," presented at Workshop on Test Methods for Silicon Feedstock Materials, Bricks and Wafers, SEMI PV Materials Standards Committee, Munich, Germany, Jun. 14, 2012, 21 pages.

Abstract of JP S6453138 A

European Search Report dated Mar. 10, 2017 for EP Application No. 16197419.1 filed on Nov. 4, 2016, 3 pages.

European Office Action dated May 3, 2017 for EP Application No. 14800193.6 filed on Oct. 29, 2014, 6 pages.

* cited by examiner

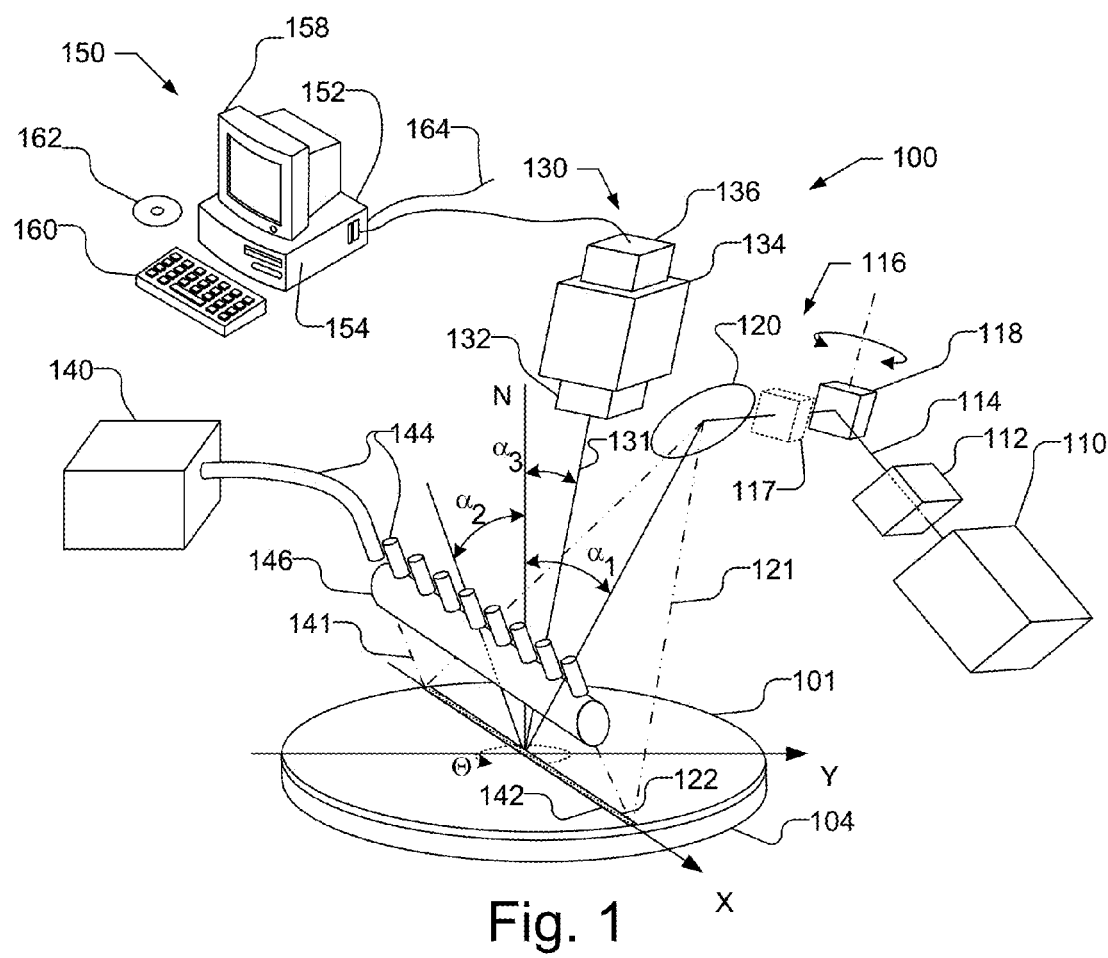
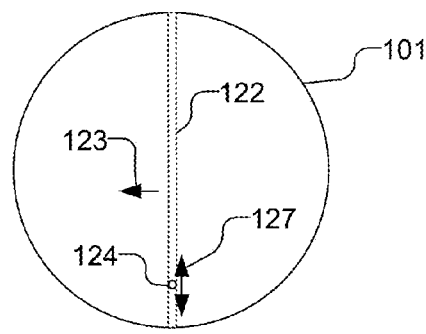 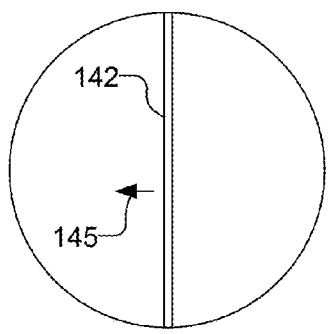
Fig. 1
Fig. 2A    Fig. 2B

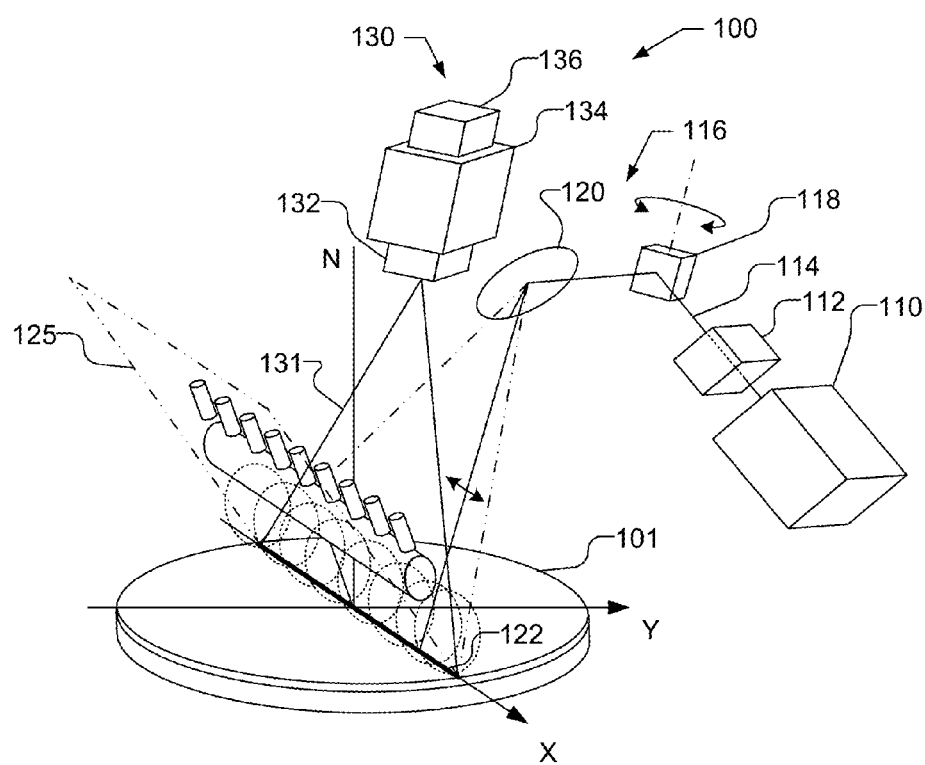
Fig. 5A
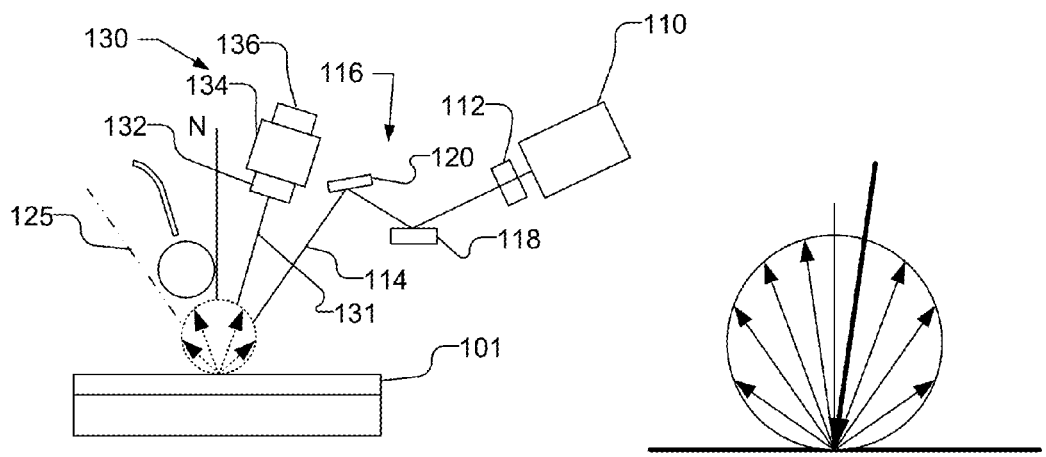
Fig. 5B
Fig. 6

OPTICAL METROLOGY SYSTEM FOR SPECTRAL IMAGING OF A SAMPLE

CROSS REFERENCE TO RELATED APPLICATIONS

This application is a continuation-in-part of U.S. application Ser. No. 14/936,635, filed Nov. 9, 2015, which is a continuation of U.S. application Ser. No. 14/091,199, filed Nov. 26, 2013, now U.S. Pat. No. 9,182,351, this application further claims priority under 35 USC 119 to U.S. Provisional Application No. 62/253,092, filed Nov. 9, 2015, all of which are incorporated by reference herein in their entireties.

BACKGROUND

Photoluminescence imaging and spectroscopy is a contactless, nondestructive method of probing the electronic structure of materials, such as silicon semiconductor wafers, solar cells, as well as other workpieces and materials. In a typical photoluminescence process, light is directed onto a wafer or other workpiece (hereinafter collectively referred to as a "sample"), where at least some of the light is absorbed. The absorbed light imparts excess energy into the material via a process of "photo-excitation." The excess energy is dissipated by the sample through a series of pathways; one such pathway is the emission of light, or photoluminescence. The intensity and spectral content of the photoluminescence is directly related to various material properties of the sample and, thus, can be used to determine certain characteristics of the sample, including defects, as discussed in U.S. Pat. No. 7,113,276B1, which is incorporated herein by reference.

Reflectance or reflectivity imaging is a contactless, nondestructive method of probing the surface with a broadband illumination source and analyzing the intensity and spectral content of the signal bounced back from the surface. The surfaces typically can be classified into specular or diffuse surfaces and real objects typically exhibit a mixture of both properties.

It is sometimes desirable, e.g., for semiconductor wafer inspection applications, to measure intensity and spectral content of the photoluminescence and reflectance of the semiconductor wafer-size workpiece for the purpose of quality inspection in the same apparatus either concurrently or in a short sequence, with single wafer load, while achieving a high measurement throughput combined with high measurement spatial and spectral resolution.

Conventionally, spectral photoluminescence or combined spectral photoluminescence and reflectance are measured using a single point-by-point inspection solution. In a point-by-point solution, the sample is placed on an X-Y motion (or R-Θ) system and is illuminated and measured at a single excitation point. The sample is moved to another measurement point and again illuminated and measured. By repeating the translation of the sample in the X-Y directions, a photoluminescence and reflectance maps could be constructed from the point-by-point measurements. This solution, however, is inherently slow and therefore impractical in the full wafer inspection systems, especially at large specimen sizes, close to and above 100 mm in diameter, due to the low throughput.

SUMMARY

An optical metrology device is capable of detection of any combination of photoluminescence light, specular reflection of broadband light, and scattered light from a line across the width of a sample. The metrology device includes a first light source that produces a first illumination line on the sample. A scanning system may be used to scan an illumination spot across the sample to form the illumination line. A detector collects the photoluminescence light emitted along the illumination line. Additionally, a broadband illumination source may be used to produce a second illumination line on the sample, where the detector collects the broadband illumination reflected along the second illumination line. The detector may also image scattered light from the first illumination line. The illumination lines may be scanned across the sample so that all positions on the sample may be measured. A signal collecting optic may collect the photoluminescence light and broadband light and focus it into a line, which is received by an optical conduit. The output end of the optical conduit has a shape that matches the entrance of the detector.

In one embodiment, an apparatus includes a light source that produces a first illumination beam; an optical system that receives the first illumination beam and produces an illumination spot on a surface of the sample; a scanning system that scans the illumination spot to form a first illumination line across the sample, wherein the scanning system scans the first illumination beam in a plane that is at a first non-normal angle of incidence on the sample, and wherein the sample emits photoluminescence light in response to excitation caused by the illumination spot along the first illumination line; a broadband light source that produces broadband light; a lens that focuses the broadband light into a second illumination line on the surface of the sample, the second illumination line overlays and is aligned with the first illumination line and is incident on the sample at a second non-normal angle of incidence that is different than the first non-normal angle of incidence, wherein the second illumination line is reflected by the sample to produce reflected light; a stage for providing relative movement between the sample and the first and second illumination lines; a detector receives the photoluminescence light emitted along the first illumination line and further receives the reflected light from the second illumination line as the stage produces relative movement between the sample and the first and second illumination lines; and a processor coupled to the detector and configured to a characteristic of the sample for a plurality of positions on the surface of the sample using the photoluminescence light and the reflected light.

In one embodiment, an apparatus that includes an illumination source that produces a first light beam; a first lens system that causes the first light beam to be incident on a surface of a sample as a first illumination line orientated along a first direction, the first illumination line being incident on the sample at a first angle of incidence, wherein the sample emits photoluminescence light in response to excitation caused by the first light beam along the first illumination line; a second illumination source; a second lens system that focuses light emitted by the second illumination source onto the sample as a second illumination line orientated along the first direction and that is overlaid on the first illumination line on the surface of the sample and that is incident on the sample at a second angle of incidence that is different than the first angle of incidence; a stage for providing relative movement between the sample and first and second illumination lines in a second direction that is different than the first direction; a detector that collects reflected light from the second illumination line and receives the photoluminescence light emitted by the sample along the first illumination line; and a processor coupled to the detector and configured to determine a characteristic of the sample for a plurality of positions on the surface of the sample using the photoluminescence light and the reflected light.

In one embodiment, an apparatus includes a light source that produces an illumination beam; an optical system that receives the illumination beam and produces an illumination spot on a surface of a sample; a scanning system that scans the illumination spot to form an illumination line across the sample, wherein the sample emits photoluminescence light in response to excitation caused by the illumination spot along the illumination line; a stage for providing relative movement between the illumination line and the sample; a signal collecting optic extending a length of the illumination line, the signal collecting optic receives the photoluminescence light from the illumination line and focuses the photoluminescence light into a line; an optical conduit having a linear reception end that receives the photoluminescence light focused by the signal collecting optic, the optical conduit further having an output end having a different shape than the linear reception end; a detector that collects the photoluminescence light from the optical conduit, the detector having an entrance aperture that matches a shape of the output end of the optical conduit; and a processor coupled to the detector to receive the photoluminescence light to determine a characteristic of the sample.

In one embodiment, a method includes illuminating a surface of a sample with a light source along an illumination line having an orientation in a first direction, wherein the sample emits photoluminescence light from the illumination line in response to excitation caused by light from the light source; collecting the photoluminescence light from the illumination line with a signal collection optic along a length of the illumination line and focusing the photoluminescence light into a line with the signal collection optic; receiving the photoluminescence light along the line with an optical conduit having a linear reception end and outputting the photoluminescence light from the optical conduit at an output end having a different shape than the linear reception end; detecting the photoluminescence light received from the output end of the optical conduit with a detector having an entrance aperture that matches a shape of the output end of the optical conduit; moving the illumination line across the surface of the sample in a second direction that is different than the first direction; and determining a characteristic of the sample for a plurality of positions on the surface of the sample using the photoluminescence light detected by the detector.

BRIEF DESCRIPTION OF THE DRAWINGS

FIG. 1 illustrates an optical metrology device capable of simultaneous detection of any combination of photoluminescence light, specular reflection of broadband light, and scattered light from a line across the width of a sample.

FIG. 2A illustrates a top view of the surface of the sample with an illumination spot from a first light source that is scanned across the width of the sample to produce an illumination line and the illumination line is moved across the sample.

FIG. 2B illustrates a top view of the sample with the illumination line from a second light source and the illumination line is moved across the sample.

FIGS. 5A and 5B illustrate a perspective view and side view, respectively, of the excitation of the sample with the scanning illumination beam and the emitted photoluminescence light collection by the optical metrology device of FIG. 1.

FIG. 6 illustrates an incident illumination beam and the Lambertian characteristic of the emitted photoluminescence light.

DETAILED DESCRIPTION

Figure 3A:
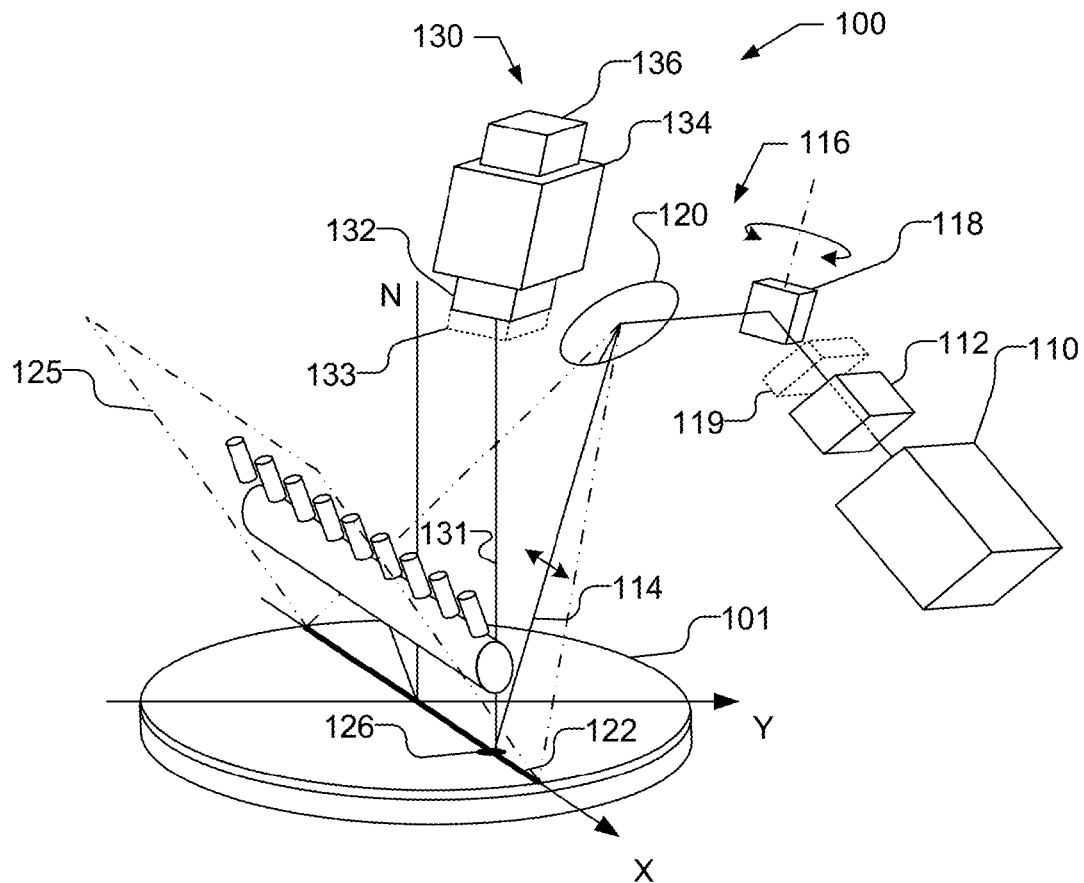
FIGS. 3A and 3B illustrate a perspective view and side view, respectively, of a dark channel observation of scattered light by the optical metrology device of FIG. 1.

FIG. 1 illustrates an optical metrology device 100 capable of simultaneous detection of any combination of photoluminescence light, specular reflection of broadband light, and scattered light from a line across the width of a sample. The sample is moved in a single direction to sweep the line across the sample so that data may be quickly collected from every position on the surface of the sample.

The metrology device 100 includes a first light source 110, which may be, e.g., a narrow band illumination source, such as a laser. By way of example, the light source 110 may be a high intensity laser, such as a Continuous Wave (CW) laser with peak wavelength at 405 nm and power in 1 mW to 500 mW range, depending on the photoluminescence efficiency of the measured sample and desired signal intensity to be recorded by the detector. If desired, more than one laser may be used to produce multiple narrow band wavelengths that are combined for light source 110. By way of example, other laser wavelengths, such as 266 nm, 355 nm, 375 nm, 532 nm, 640 nm or 830 nm, and others not listed here, may additionally or alternatively be used, either individually or selectively combined. Laser(s) used as light source 110 may operate either in Continuous Wave or Q-Switched mode of operation. If the Q-Switched (QS) laser is used for sample excitation, the instantaneous power, i.e. power during the pulse, may be much higher, e.g., in a few (2.5 kW) kilowatt range.

A lens system including optics 112 is used to produce an illumination spot with the illumination beam 114 on the surface of the sample 101. The illumination spot produced by the illumination beam 114 should have a size and/or power density to excite photoluminescence in the sample 101. By way of example, the illumination spot size may be between 50 μm to 1 mm range and/or have a power density of between approximately 0.1 W/cm$^2$ to 10$^8$ W/cm$^2$ range. For example, if a CW 1 mW laser is focused to about a 1 mm spot, the power density is about 0.127 W/cm$^2$. The same CW 1 mW laser focused to 50 micron spot will give power of 50 W/cm$^2$. If a higher power 500 mW CW laser is used, and is focused to a 1 mm spot, a power density of 63 W/cm$^2$ is reached and the same laser focused to 50 μm will lead to the power density of 2.5*10$^4$ W/cm$^2$. Thus, typical power densities for CW lasers are in 0.1 W/cm$^2$ to 2.5*10$^4$ W/cm$^2$ range. With the use of Q-Switched lasers for sample excitation, the power densities are much different. For example, at an average power of 1 mW, and pulse duration of 10 nanoseconds (10*10$^{-9}$ s) and repetition rate of 100 kHz, the momentary power may be as high as 1 W and the corresponding power density at a 1 mm spot is 127 W/cm$^2$. When the same laser is used with an average power of 500 mW, and is focused to 50 μm spot size, the momentary power may reach, e.g., 2.5*10$^7$ W/cm2.

The lens system may further include a scanning system 116, illustrated as including a scanning mirror 118 and a fixed mirror 120, that is used to scan the illumination spot across the width of the surface of the sample 101 as an illumination line 122, that is illustrated as being orientated along the X direction. The scanning speed/frequency of scanning system 116 may be adjusted depending on the scan resolution and sensor read-out speed. For example, the frequency may be, e.g., between 50-100 Hz range, but may vary in a range of 1 Hz to 10 kHz or more. The scanning mirror 118 moves to scan the illumination spot across the surface of the sample 101 and may be, e.g., a (swinging) galvanometric mirror or a rotating polygonal mirror. FIG. 2A, by way of example, illustrates a top view of the surface of the sample 101 with an illumination spot 124, produced by illumination beam 114 (FIG. 1) that is scanned across the width of the sample, as indicated by arrows 127. As illustrated, by lines 121 in FIG. 1, the scanning system 116 scans the illumination beam 114 across the sample 101 within a plane, which creates a non-zero angle of incidence α1, with respect to surface normal N. Thus, the illumination line 122 is incident on the surface of the sample 101 at a non-normal angle of incidence. It should be understood that the illumination line 122 is additionally scanned across the surface of the sample 101 by the stage 104 (FIG. 1) moving the sample 101 along the Y direction, as illustrated by arrow 123, so that the illumination line 122 may be incident on all positions on the surface of the sample 101.

It should be understood that FIG. 1 illustrates one configuration of the narrow band illumination source 110 and associated optics, including scanning system 116, but that other configurations may be used if desired. For example, while the use of fixed mirror 120 is advantageous to simplify system alignment, if desired, the fixed mirror 120 may be removed from scanning system 116, with the light source 110, lens 112, and scanning mirror 118 repositioned so that the illumination beam 114 illuminates the sample 101 directly, without the need for the redirecting mirror 120. Moreover, it should be understood that the optics 112 may focus the illumination beam 114 into an illumination spot 124 on a surface of the sample 101. If the illumination beam 114 is focused at a sample plane, which is coincident with the surface of the sample 101, the illumination spot may become slightly defocused as the illumination beam moves along the illumination line 122, but the signal intensity variations caused by the defocusing can be compensated by signal processing within computer 150. Alternatively, by way of example, the optics 112 may collimate the illumination beam 114. If desired, the collimated illumination beam 114 may be focused on the surface of the sample using an optional F-theta lens 117, shown with dotted lines in FIG. 1. Moreover, if desired, the collimated illumination beam 114 may be incident on the surface of the sample 101 as the illumination spot without being focused, with an associated loss of resolution and excitation conditions.

By scanning the illumination spot 124 across the sample 101 to produce the illumination line 122, a high power density of the incident light may be maintained. Consequently, the illumination beam from light source 110 imparts energy into the material of the sample via "photo-excitation" thereby producing photoluminescence light emitted from the sample along the illumination line 122. Additionally, surface defects on the sample 101, such as scratches, particles, epitaxial growth defects, e.g., stacking faults or mounds, may scatter the illumination beam 114 as it is scanned along the illumination line 122.

As illustrated, by lines 121 in FIG. 1, the scanning system 116 scans the illumination beam 114 across the sample 101 within a plane, which creates a non-zero angle of incidence α1, with respect to surface normal N. Thus, the illumination line 122 is incident on the surface of the sample 101 at a non-normal angle of incidence.

The optical metrology device 100 includes a detector 130 that receives light from the surface of the sample 101 along a detector path 131 that has a non-zero angle α3 with respect to surface normal N. Thus, as illustrated in FIG. 1, the detector 130 has viewing angle α3 that is different than the angle of incidence α1 of the illumination line 122. As a result, the specular reflection of the illumination beam 114 from the surface of the sample 101 does not enter the detector path 131. Typically, the photoluminescence signal is a few orders weaker than the reflected radiation signal. With the use of the angle of incidence α1 and the viewing angle α3, the optical metrology device 100 permits the illumination beam 114 to reflect from the specular surface of the sample 101 without interfering with the photoluminescence signal received by the detector 130, thereby avoiding the need for filtering the reflection of the illumination beam 114. Moreover, because the illumination beam 114 is not filtered, the detector 130 may receive light scattered by surface defects without receiving illumination beam 114, i.e., enabling dark field observations. It should be understood that the photoluminescence light produced by the sample 101 in response to excitation by the illumination beam 114 will have a different wavelength(s) than the illumination beam 114 itself. Accordingly, the wavelengths from the photoluminescence light and the scattered light can be dispersed into different spectral channels. Consequently, the optical metrology device 100 may be used for simultaneous detection of surface topographical defects and photoluminescence. Additionally, with the use of the scanning system 116, the light source 110 may function as a line illumination source without loss of power density or illumination uniformity along the line if a cylindrical lens or cylindrical mirror were used.

The detector 130 includes optics 132, a spectrometer 134, and a sensor 136 that includes a two-dimensional CCD or CMOS sensor array. The light collected along the detector path 131, e.g., photoluminescence light or scattered light, is collected by the fore optics 132, then passes through a narrow entrance slit aperture in the spectrometer 134. The field of view of the spectrometer 134 is limited by the entrance slit, which matches the orientation of the illumination line 122. Thus, the entrance slit of the detector 130, or to be more exact, the spectrometer 134, is aligned with the illumination line 122 and overlaying broadband illumination line 142 (discussed below), i.e. the entrance slit and illumination lines 122 and 142 all belong to the same plane, while illumination line 122 and 142 are overlaid on top of each other and the entrance slit to the detector 130 is parallel to the illumination lines 122 and 142. The spectrometer 134 disperses the spectrum of the received light and the sensor 136 at the exit of the spectrometer 134 records with a two dimensional (2D) sensor array and produces a resulting image frame, with a first dimension of the sensor array representing the spatial position along the illumination line 122 and the second dimension of the sensor array representing spectral information. The spectrometer 134 separates the wavelengths of emitted photoluminescence light and separates the scattered light along one dimension of the 2D sensor array, while the position along the illumination line 122 is recorded by the second dimension of the 2D sensor array. For example, one point along the illumination line 122 may emit a maximum photoluminescence at 460.3 nm, while another point on the illumination line 122 may emit a maximum photoluminescence at 460.8 nm. Thus, the spectrometer 134 separates the wavelengths of the emitted photoluminescence light to perform spectral photoluminescence imaging.

The metrology device 100 further includes a second light source 140, which may be, e.g., a broadband illumination source, such as a halogen light source, that includes wavelengths of light that differ from the wavelengths used by the first light source 110 or the wavelengths of photoluminescence light emitted by the sample 101 in response to excitation by the illumination beam 114. The broadband radiation source (sometimes referred to as a "white" light source) is formed into the illumination line 142 which is aligned with and overlays the illumination line 122 on the surface of the sample 101. As illustrated, the illumination line 142 may be produced, e.g., using a series of optical fibers 144 (only one of which is illustrated as coupled to the light source 140). By way of example, the second light source 140 with the series of optical fibers 144 may be a Lightline product manufactured by Schott North America, Inc. The light from the multiple optical fibers 144 is formed into a nearly collimated line-like beam with a cylindrical lens 146. FIG. 2B illustrates a top view of the sample 101 with the illumination line 142 from the second light source 140.

As illustrated in FIG. 1, the broadband light from light source 140 illuminates the surface of the sample 101 along a plain, illustrated by lines 141 that is at a non-zero angle of incidence $\alpha 2$, with respect to surface normal N. Thus, the illumination line 142 is incident on the surface of the sample 101 at a non-normal angle of incidence $\alpha 2$. It should be understood that the illumination line 142 is additionally scanned across the surface of the sample 101 (along with overlaid illumination line 122) by stage 104 (FIG. 1), as illustrated by arrow 145 in FIG. 2B, so that the illumination line 142 may be incident on all positions on the surface of the sample 101. The angle of incidence $\alpha 2$ is different from the angle of incidence $\alpha 1$ and has a sign that is different from the sign of angle $\alpha 1$, i.e., the illumination line 142 is incident on the surface of the sample from an opposite direction as the illumination line 122, and has a different angle of incidence. The angle of incidence $\alpha 2$ of the illumination line 142, however, is equal, but opposite in value, as the viewing angle $\alpha 3$ of the detector path 131, i.e., viewing angle $\alpha 2 = -\alpha 3$. Thus, the detector 130 viewing angle is tuned to the incident angle of the illumination line 142 and as a result, the specular reflection of the broadband light along illumination line 142 is also aligned with the field-of-view of the spectrometer 134. Thus, both the illumination line 122 produced by light source 110 and the illumination line 142 produced by the light source 140 are received by the detector. The spectrometer 134 separates the wavelengths of the specular reflection of the broadband illumination along the illumination line 142 into one dimension of the 2D sensor array, while the position along the illumination line 142 (and the illumination line 122) is represented by the second dimension of the 2D sensor array.

The broadband light source 140 may use wavelengths of light that are different than the wavelength(s) used by the first light source 110 and wavelength(s) of the photoluminescence light emitted by the sample 101 so that the spectrometer 134 may separate the wavelengths from the reflected broadband light from the wavelengths of the scattered light and the wavelengths of the photoluminescence lights. Accordingly, the first light source 110 and second light source 140 may be used with the detector 130 to simultaneously detect the spectral information with respect to position along with illumination lines 122 and 142 for the photoluminescence light caused by the excitation of illumination beam 114, the dark field scattering of the illumination beam 114, as well as the bright field reflectance from the light source 140. By way of example, the optical metrology device 100 may use a range of wavelengths between 400-1,000 nm (i.e. 600 nm range), based on the wavelengths of the narrow band light source 110, the broadband light source 140, and the emitted photoluminescence light. The detector 130 may separate the received light into, e.g., 1200 wavelengths, i.e., number of pixels in the spectral dimension of the sensor array, and thus, the detector 130 may have a spectral resolution of 0.5 nm. Of course, if desired, other spectral resolutions may be used, as well as wavelengths of light or ranges of wavelengths of light, as well as the number of wavelengths detected by detector 130.

Moreover, the broadband light that is specularly reflected from the surface of the sample 101 is directed to the detector 130 without any need for mechanical repositioning of the detector 130, therefore the detector 130 can collect the surface reflectance, scattering and photoluminescence signals concurrently or in a quick succession without any delay for mechanical repositioning of any apparatus optics subcomponents. Of course, if desired, the first light source 110 and second light source 140 may be used in quick succession so that the detector 130 does not simultaneously receive light from both illumination lines 122 and 142.

The sample 101 is held on a linear stage 104 that can translate the sample 101 in a direction that is different than the orientation of the illumination lines 122 and 142. For example, the orientation of the illumination lines 122 and 142 may be in a direction (e.g., the X-direction) that is orthogonal to the direction of travel of the linear stage 104 (e.g., the Y-direction). The stage 104 translates the sample 101 to place the illumination lines 122 and 142 at multiple positions across the sample 101 (as illustrated by arrows 123 and 145 in FIGS. 2A and 2B) and the spectral imaging of the illumination lines 122 and 142 is repeated at each new position. The process of imaging and moving the sample 101 is repeated to scan the illumination lines 122 and 142 across the sample 101 thereby producing a series of 2D image frames. If desired, the stage 104 may move the sample 101 in steps or move the sample 101 continuously so that data acquisition is performed continuously (e.g., with a high frequency scan of the illumination spot 124), without the Y-axis motion stopping at each line. For example, when a high frequency scan (e.g., 500 Hz) of the illumination spot 124 is used with a relatively low speed stage motion along the Y-axis and low speed collection of image frames (e.g., 100 Hz), the illumination beam 114 is scanned over the illumination line 122 several times for each given image frame, e.g., five times in the given example, which provides for improved signal averaging. The speed of the stage motion along Y axis may be expressed in millimeters per second and depends on the desired resolution along the Y direction. For example, when the Y speed is 20 mm/s and the frame rate is 100 frames per second, the Y resolution is 20 mm/s divided by 100/s equals 0.2 mm.

Thus, in one data capture operation, the optical metrology device 100 is able to collect concurrently the spectral photoluminescence and spectral scattered radiation and spectral reflected radiation signals from the line-illuminated portion of the sample 101, and may move in a single axis and repeatedly perform the data capture operation to acquire data for the entire sample surface. In one embodiment the data for the entire sample surface is obtained by moving the sample 101 underneath of the illumination lines 122 and 142 with a linear stage in the Y-direction. In another embodiment, however, the data can be collected by rotating the sample 101 underneath of the illumination lines 122 and 142 with a rotary stage in Θ (angle) direction, illustrated in FIG. 1 with a dotted arrow. In both embodiments, the sample 101 is moved in one axis only, either Y or Θ (both are not required), resulting with a high speed measurement. In comparison, conventional systems acquire data from a single illumination spot and must move the sample in two axes to acquire data for the entire sample surface. Thus, the optical metrology device 100 uses a single unidirectional stage, as opposed to the conventional two linear or linear and rotary stage systems. Moreover, data acquisition is accelerated because of the elimination of required stage motion along the X-axis.

It should be understood the motion between the illumination lines 122 and 142 and sample 101 is relative, and thus, if desired, the stage 104 may be held stationary and the illumination lines 122 and 142 may be moved (laterally in the Y direction or rotated in the Θ direction using a stage to move, e.g., the light sources and associated optics with respect to the sample 101, or other appropriate means.

The plurality of image frames produced by the detector 130 as the sample 101 is moved and spectral information from the line-illuminated portions of the sample 101 is acquired may be received by a computer 150, which may store the plurality of image frames as three dimensional (3D) data cube. The 3D data cube includes two dimensions that are spatial (e.g., one dimension is the position along the illumination lines 122 and 142 (X axis) and the other dimension is the position of the line scanned across the sample (Y axis)) and a third dimension represents the spectral information. The detector 130 is coupled to provide the image data to the computer 150, which includes a processor 152 with memory 154, as well as a user interface including e.g., a display 158 and input devices 160. A non-transitory computer-usable medium 162 having computer-readable program code embodied may be used by the computer 150 for causing the processor to control the metrology device 100 and to perform the functions including the analysis described herein. The data structures and software code for automatically implementing one or more acts described in this detailed description can be implemented by one of ordinary skill in the art in light of the present disclosure and stored, e.g., on a computer readable storage medium 162, which may be any device or medium that can store code and/or data for use by a computer system such as processor 152. The computer-usable medium 162 may be, but is not limited to, magnetic and optical storage devices such as disk drives, magnetic tape, compact discs, and DVDs (digital versatile discs or digital video discs). A communication port 164 may also be used to receive instructions that are used to program the computer 150 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

By way of example, the computer 150 may use the photoluminescence signals received from the detector 130 for each position on the surface of the sample 101 as stored in the 3D data cube and generate a photoluminescence image (or map) of the sample 101. The photoluminescence image may be, e.g., a map of signal intensity of the photoluminescence signal. Inspection of the photoluminescence intensity image may be used for process control to assure that all portions of the sample 101 meet desired specifications. For example, where the sample 101 contains manufactured light emitting diodes (LEDs) chips, inspection of the photoluminescence data, e.g., in the form of a photoluminescence intensity image, can be used to assure each LED will have appropriate brightness. Similarly, the photoluminescence intensity image may be used for defect segmentation and predicting yield losses based on presence of localized low photoluminescence signals, which can lead to out-of-specification device at the Back-End of Line. If desired, the photoluminescence signal may be processed to produce other images or maps. For example, a Peak Lambda image may be produced to show the distribution of Peak Lambda over the sample surface, where Peak Lambda is the wavelength at which any given point in the image or map has maximum photoluminescence. Thus, for example, one point on the sample surface may emit maximum photoluminescence at 460.3 nm, while another point on the surface of the same sample may emit a maximum photoluminescence at 460.8 nm, which can be clearly seen with a Peak Lambda image. With the use of the spectral photoluminescence imaging, the different wavelengths of photoluminescence light emitted by the sample may be identified. Accordingly, the optical metrology device 100 may be used for process control to assure that all points on the sample surface emit photoluminescence within a predefined wavelength range. Additionally or alternatively, the photoluminescence signal can be transformed into a Full-Width-Half Maximum (FWHM) image, which shows the FWHM value for each Peak Lambda at any given point on the sample. The FWHM image, by way of example, may be used to assure that light emitting diodes (LEDs) that are manufactured with the sample emit light within predefined-width (band) spectral range. The photoluminescence signal may be processed to produce images of the sample 101 other than the photoluminescence intensity, Peak Lambda and FWHM images. For example, the photoluminescence signals may be processed or analyzed to produce different qualities, such as, e.g., a map of photoluminescence intensity at a given fixed wavelength, which is different than the maximum photoluminescence intensity map. Moreover, images or maps of interest may be produced by combining sets of images, such as those discussed, e.g., by pixel-by-pixel multiplication. Thus, the photoluminescence signal may be processed to produce other desired images of the sample 101 based on the recorded photoluminescence signals or analyzed in other ways for process control during manufacture of the sample.

Additionally, the computer 150 may process the received reflected broadband signal to determine a characteristic of the sample 101 at multiple positions and produce a map of that characteristic. For example, layer thickness may be calculated based on the spectral response associated with reflection of the broadband light, and thus, the received reflected broadband signal may be used to determine thickness for points on the sample surface and an epilayer thickness image (or map) may be produced. Thus, the optical metrology device 100 may be used to monitor the epitaxial layer thickness at any given point on the surface of the sample, which may be used to assure that the measured thickness is within predefined range for a given epitaxial growth process. Additionally, using the received scattered light, the computer 150 may produce a darkfield image of the surface of the sample 101, thereby exposing surface defects, which may be related scratches, particles, epitaxial growth defects, e.g., stacking faults or mounds, etc.

Figure 3B:
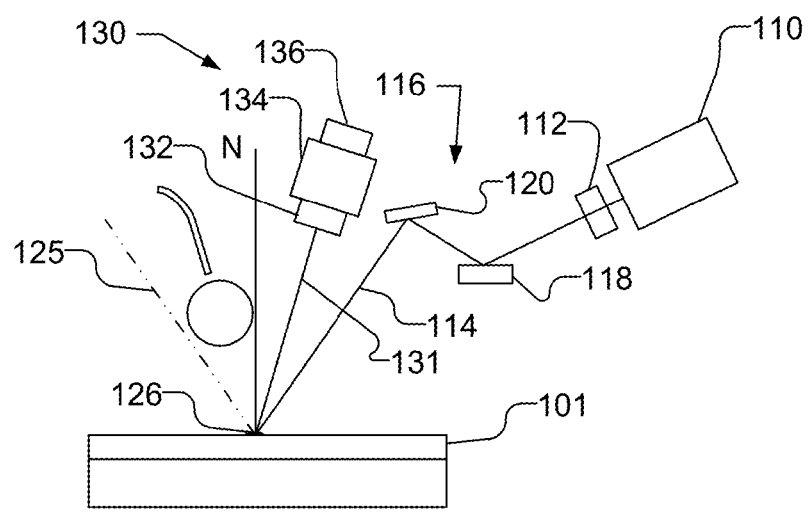

FIGS. 3A and 3B illustrate a perspective view and side view, respectively, of the dark channel observation of scattered light by optical metrology device 100. As illustrated, the light source 110 produces illumination line 122 on the surface of the sample 101 using the optics 112 and scanning system 116, including scanning mirror 118 and fixed mirror 120. If the sample were defect free, light would be specularly reflected by the surface of the sample 101, as illustrated by lines 125, and would not be detected by the camera sensor 136. When a surface defect 126 is present on the sample 101, a portion of the illumination beam 114 is scattered when the illumination beam 114 is scanned over the defect 126. The scattered light along the detector path 131 received by the detector 130 and enters the spectrometer 134 through the slit aperture. The field of view of the spectrometer 134 is limited by a slit aperture, and therefore, the sensor 136 only images the illumination line 122. The specular reflection of the illumination beam 114 is not received by the spectrometer 134. The spectrometer 134 normally separates light into wavelength bins in the spectral dimension of the 2D sensor array. The scattered light, however, originates from the narrow band light source 110 and, thus, the scattered received by detector 130 is deflected by the spectrometer 134 into the bin(s) corresponding to the wavelength(s) of the light source 110, which is recorded by the sensor 136. The performance of the scattered light channel may be further altered by adding light polarizer and analyzer into the optical path of the narrow band illumination beam 114. By way of example, a beam polarizer 119 may optionally be placed downstream of the light source 110, e.g., between the lens 112 and mirror 118, and the analyzer 133 may be combined with the fore optics 132.

Figure 4A:
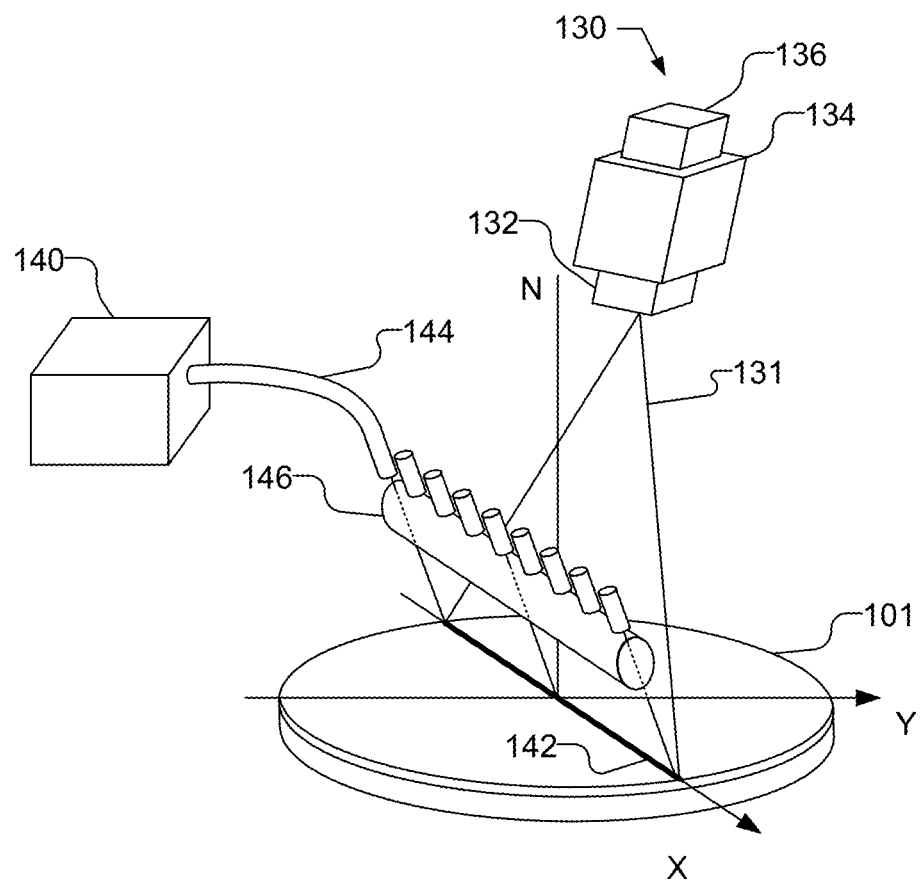
FIGS. 4A and 4B illustrate a perspective view and side view, respectively, of the bright field reflectance observation by the optical metrology device of FIG. 1, with a narrow band light source and associated optics omitted for clarity.
Figure 4B:
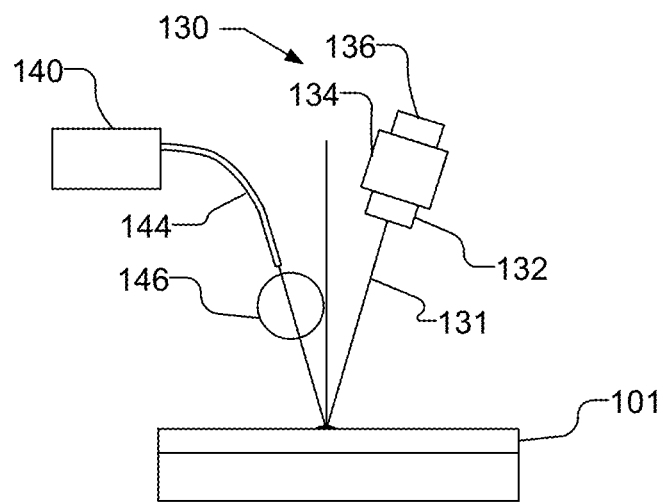

FIGS. 4A and 4B illustrate a perspective view and side view, respectively, of the bright field reflectance observation by optical metrology device 100, omitting the light source 110 and associated optics for clarity. The broadband light source 140 illuminates the sample 101 along the illumination line 142 line extending across the width of the sample 101 along an orientation that matches the orientation of the entrance slit of the spectrometer 134. As a result, the light from the light source 140 that is specularly reflected from the surface of the sample 101 enters the spectrometer 134 through the slit aperture. Within the spectrometer 134, the broadband light is separated (binned) into a series of wavelengths, which are recorded by 2D sensor array in the sensor 136, with one dimension of the 2D sensor array representing the spectral information and the other dimension representing the spatial information along the illumination line 142. The arrangement of the broadband light source 140, thus, is a bright field mode of operation in which an illumination line 142, which may be the width of the sample 101, is spectrally imaged. The use of a non-normal angle of incidence for the bright field observation advantageous simplifies uniform illumination and spectroscopic imaging of the sample 101 along illumination line 142.

FIGS. 5A and 5B illustrate a perspective view and side view, respectively, of the excitation of the sample 101 with the scanning illumination beam 114 and the emitted photoluminescence light collection by optical metrology device 100. Similar to FIGS. 3A and 3B above, the light source 110 produces illumination line 122 on the surface of the sample 101 using the optics 112 and scanning system 116, which may include scanning mirror 118 and fixed mirror 120. As discussed above, fixed mirror 120 may be removed or replaced and/or a F-Theta lens may be used. The light from illumination beam 114 that is specularly reflected is illustrated by lines 125. Another portion of the light from illumination beam 114, however, enters the sample 101 and is absorbed. The absorbed energy generates electron-hole pairs, which upon recombination emit photoluminescence light along the excitation line, i.e., illumination line 122. The generated photoluminescence light emitted from the excitation line exits the sample 101 at multiple directions with near Lambertian characteristics. FIG. 6, by way of example, illustrates the incident illumination beam 114 and the Lambertian characteristic of the emitted photoluminescence light (the specularly reflected light is not illustrated in FIG. 6). In addition, because the illumination beam 114 is scanned across the width of the sample 101 along illumination line 122, the photoluminescence light is emitted along the excitation direction, as illustrated in FIG. 5A. The emitted photoluminescence light along the detector path 131 is received through the slit aperture of the spectrometer 134, where the light is deflected by the spectrometer 134 into the bin(s) corresponding to the wavelength(s) of the photoluminescence light, which is recorded by the sensor 136.

Figure 7:
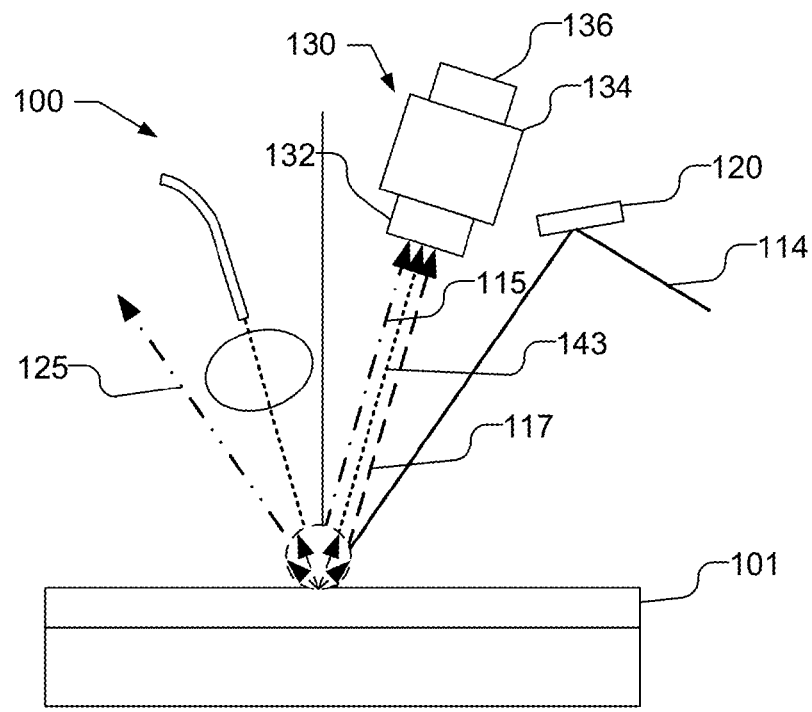
FIGS. 7 and 8 illustrate a side view (along the Y-Z plane) and a front view (along the X-Z plane), respectively, illustrating the simultaneous collection of dark field scattered radiation, bright field reflectance radiation and photoluminescence light by the optical metrology device of FIG. 1.
Figure 8:
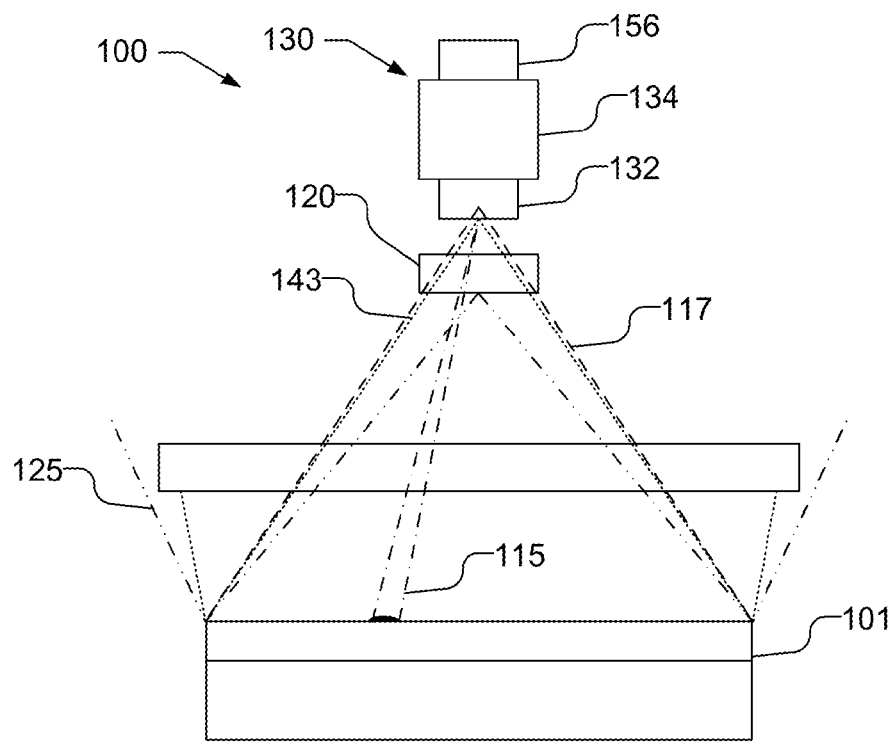

FIGS. 7 and 8 illustrate a side view (along the Y-Z plane) and a front view (along the X-Z plane), respectively, illustrating the simultaneous collection of dark field scattered radiation, bright field reflectance radiation and photoluminescence light by the optical metrology device 100. As illustrated, the illumination beam 114 generates scattered light 115, and excites photoluminescence light 117, that are received by the spectrometer 134, along with the reflected broadband light 143.

Figure 9:
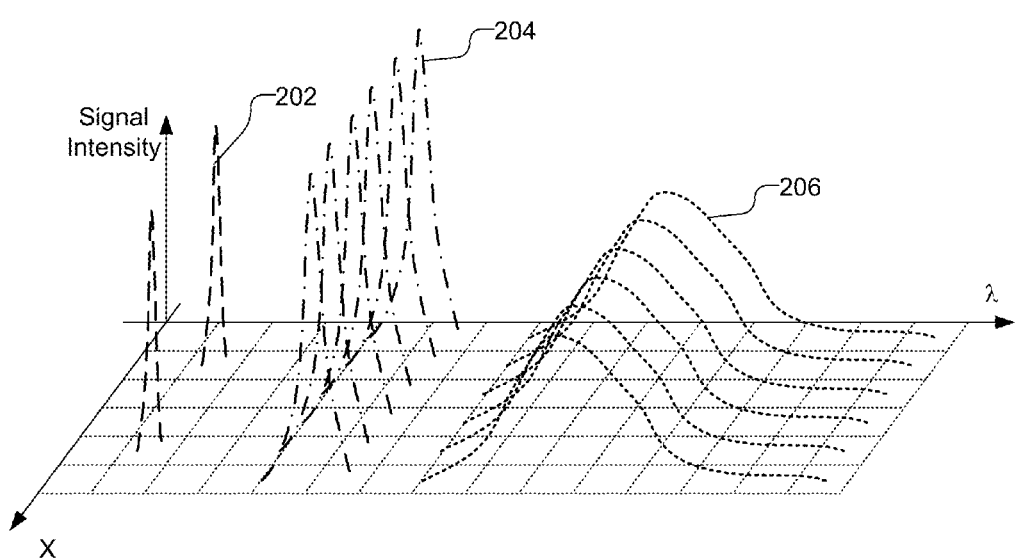
FIG. 9 illustrates the signal separation of the three spectral channels (dark field scattered radiation, bright field reflectance radiation, and photoluminescence light) imaged by a 2D sensor array.

FIG. 9, by way of example, illustrates the signal separation of the three spectral channels (dark field scattered radiation, bright field reflectance radiation, and photoluminescence light) imaged by the 2D sensor array of sensor detector 136. As illustrated, the 2D sensor array includes a first dimension (the X axis in FIG. 9) representing the spatial information along the illumination lines 122 and 142, with the other dimension representing the spectral information, i.e., wavelength λ, with respect to the signal intensity. In FIG. 9, the scattered laser beam signal is illustrated by peaks 202, the photoluminescence signal is illustrated by peaks 204, and the reflected broadband beam signal is illustrated by peaks 206.

Thus, as illustrated in FIGS. 7, 8, and 9, the detector 130 can simultaneously record the photoluminescence light generated in the sample 101 in response to excitation by the illumination beam 114 and a bright field reflection of the broadband light 143. If desired, the detector 130 may further record a dark field scattering of the illumination beam 114 by defects on the sample so that, if desired, three separate signals are simultaneously imaged. The three signals may be recorded simultaneously along the entire width of the sample 101 in a macroscopic mode, as opposed to being recorded point-by point or within a narrow field of view in a microscopic as is conventionally performed. Moreover, one detector 130 is used to collect all three signals, so that there is no spatial or time shifts between the three signals. A spectrometer 134 separates the signals into three different spectral information channels, i.e., signals are spectrally separated that are recorded in different wavelength bins (sensor pixels) with the 2D sensor array sensor of the detector 130. It should be understood that the image frame illustrated in FIG. 9 is for one position of the illumination lines 122 and 142 along the Y axis in FIG. 1 and that as the stage 104 moves the sample 101 in the Y direction to scan the illumination lines 122 and 142 across the sample, the sensor 136 will produce a plurality of image frames for each position of the illumination lines 122 and 142 along the Y axis in FIG. 1.

Figure 10:
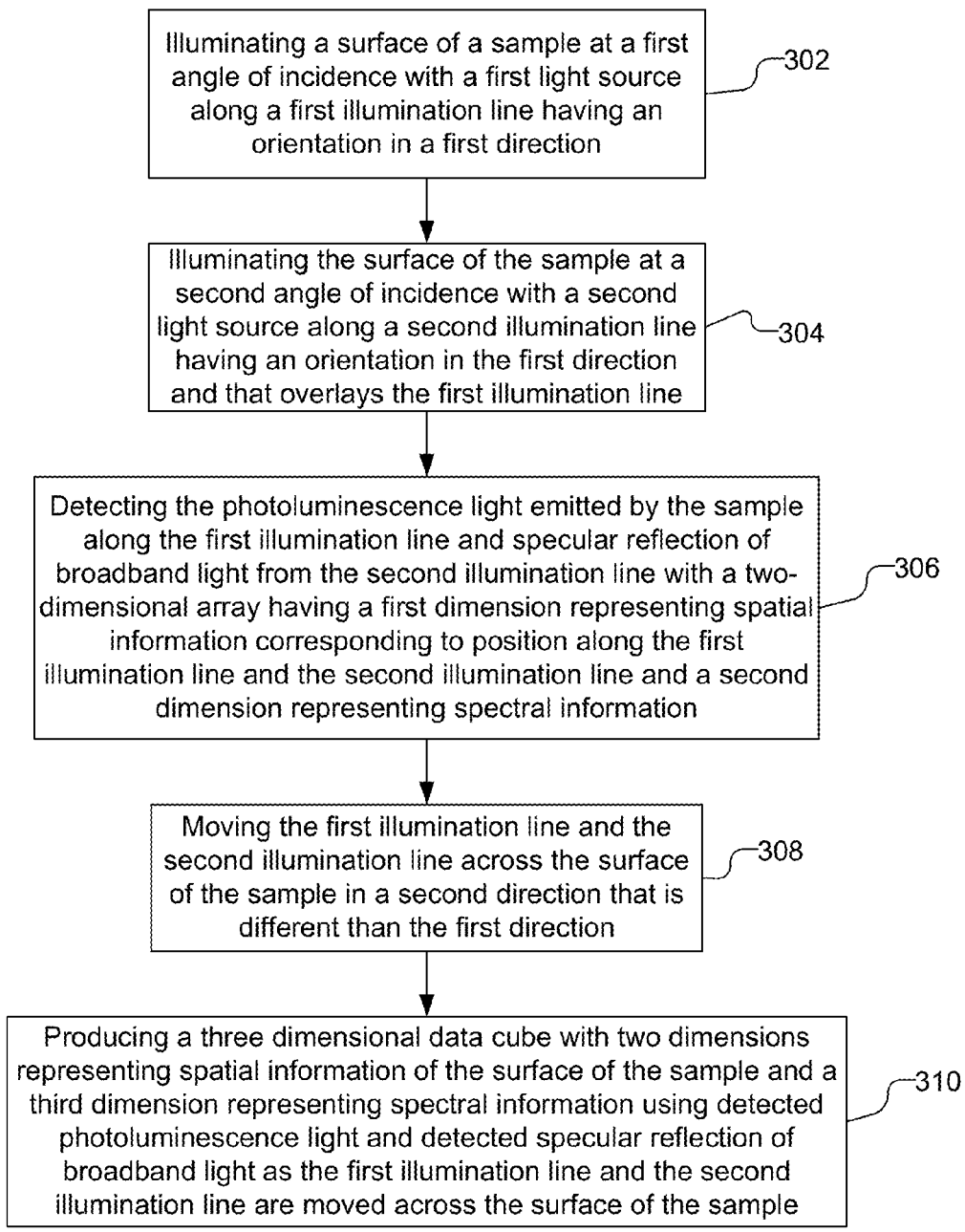
FIG. 10 is a flow chart illustrating a method of optical metrology data from a number of light sources.

FIG. 10 is a flow chart illustrating a method of optical metrology data from a number of light sources. As illustrated, a surface of a sample is illuminated at a first angle of incidence with a first light source along a first illumination line having an orientation in a first direction (302). The sample emits photoluminescence light from the first illumination line in response to excitation caused by light from the first light source. By way of example, as discussed above, the sample may be illuminated with an illumination beam produced, e.g., using a narrow band light source 110, and that is scanned across the sample to produce the first illumination line. The surface of the sample is illuminated at a second angle of incidence with a second light source along a second illumination line having an orientation in the first direction and that overlays the first illumination line (304). The second angle of incidence is different than the first angle of incidence, and the second light source is a broadband light source. The broadband light is reflected from the surface of the sample. The photoluminescence light emitted by the sample along the first illumination line and specular reflection of broadband light from the second illumination line is detected with a two-dimensional array having a first dimension representing spatial information corresponding to position along the first illumination line and the second illumination line and a second dimension representing spectral information (306). The specular reflection of light from the first light source along the first illumination line may not be detected. The first illumination line and the second illumination line, which are overlaid, are moved across the surface of the sample in a second direction that is different than the first direction (308). For example, the first direction and second direction may be orthogonal. Movement of the first illumination line and the second illumination line may be caused by a linear stage or a rotary stage moving the sample 101 with respect to the illumination lines. If desired, movement of the first illumination line and the second illumination line may be caused by a stage moving the first illumination line and the second illumination line with respect to the sample 101, e.g., by moving the light sources and associated optics with respect to the sample 101 which may be held stationary. A three dimensional data cube with two dimensions representing spatial information of the surface of the sample and a third dimension representing spectral information is produced using detected photoluminescence light and detected specular reflection of broadband light as the first illumination line and the second illumination line are moved across the surface of the sample (310).

Additionally, as discussed above, a portion of the light from the first light source may be scattered off surface defects on the sample as scattered light and the scattered light may be detected with the two-dimensional array, where the three dimensional data cube additionally includes the detected scattered light. Using the scattered light in the three dimensional data cube, a surface defect image of the surface of the sample may be produced. Additionally, a photoluminescence image of the surface of the sample may be produced using the detected photoluminescence light in the three dimensional data cube. For example, the photoluminescence image of the surface of the sample may be, e.g., a photoluminescence intensity image, photoluminescence Peak Lambda image, or a photoluminescence Full-Width-Half Maximum (FWHM) image. Additionally, a characteristic of the sample may be determined for a plurality of positions on the surface of the sample using the detected specular reflection of broadband light in the three dimensional data cube, and an image of the surface of the sample may be generated using the characteristic of the sample for the plurality of positions. For example, the epilayer thickness of the sample 101 may be determined at a plurality of locations on the surface of the sample 101 and an epilayer thickness image (or map) may be produced. As discussed above, the data from the three dimensional data cube may be analyzed for process control during manufacture of the sample.

Figure 11:
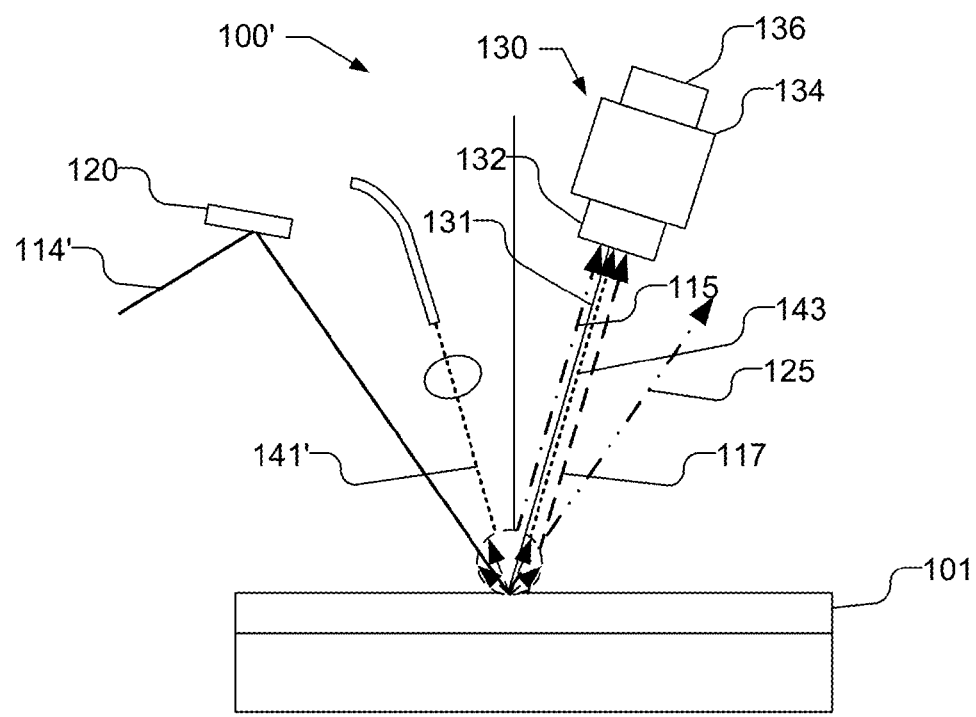
FIGS. 11 and 12 illustrate side views (along the Y-Z plane) of alternative configurations of the optical metrology device from FIG. 1.
Figure 12:
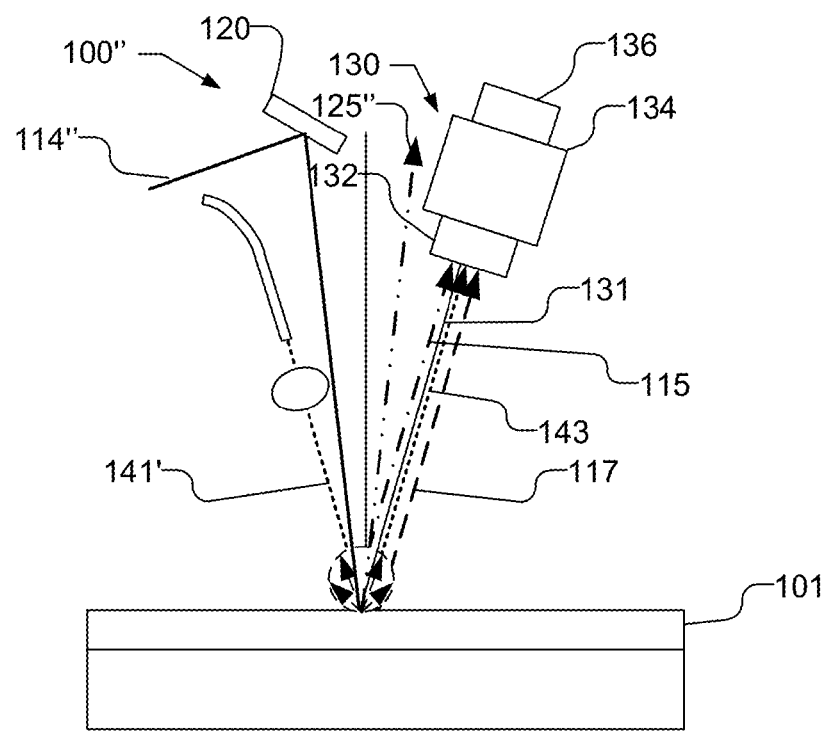

FIG. 11, by way of example, illustrates a side view of an optical metrology device 100', that is similar to the optical metrology device 100 illustrated in FIG. 7, except that the narrow band illumination beam 114' is illustrated as being incident from the same side of normal N as the broadband illumination 141'. Thus, while the narrow band illumination beam 114' and broadband illumination 141' are incident on the surface of the sample 101 from the same side of normal N, they use different angles of incidence, so that the specular reflection 125' of the narrow band illumination 114' is not along the detector path 131, thereby enabling dark field mode measurement. As can be seen in FIG. 11, the angle of incidence of the illumination beam 114' is greater than the angle of incidence of the broadband illumination 141', with respect to normal N, but this is not strictly required. FIG. 12, by way of example, is similar to FIG. 11, and illustrates an optical metrology device 100" that is configured so that the narrow band illumination beam 114" has a smaller angle of incidence compared to the broadband illumination 141', with respect to normal N, while the specular reflection 125" of the narrow band illumination 114" is still not along the detector path 131, thereby enabling dark field mode measurement.

A significant challenge for wafer inspection equipment designers is the full wafer imaging of photoluminescence or reflected or scattered light at high resolution (on the order of hundred microns per pixel) at high speed (several dozens of wafers per hour) and with high signal collection efficiency. In order to achieve high measurement speed, low numerical aperture (NA) objective lenses and large field-of-view (FOV) arrangements are sometimes used to enable signal collection from the entire sample size in one signal capture. Per common definition, numerical aperture equals NA=n*sin(θ) where n is the index of refraction of the medium where the lens is used (1.00 for air) and θ is the maximal half-angle of light which can enter the lens through its aperture. Therefore, for typical large FOV imaging system, with a 20 mm diameter lens and typical object to lens distance of about 400 mm, the numerical aperture can be calculated as NA=0.025. Low NA objective lenses and large FOV arrangements leads to low signal collection efficiency and low instrument sensitivity, because in such an arrangement, the optics-to-sample distance must be large. A large optics-to-sample distance leads to a substantial loss of photoluminescence or scattered light radiation. Higher numerical aperture objective lenses allow for shorter optics-to-sample distances, better signal collection and higher instrument sensitivity, however, at expense of reducing the FOV of the optics. As a result, the measurement speed is low because several measurements and image stitching must be applied for reconstructing information at the full sample scale.

The above-described embodiments provide a high measurement resolution and high speed by exciting the sample with a laser beam by scanning the illumination spot across the surface, e.g., using a galvanometric mirror or a rotating polygonal mirror, while probing the photoluminescence or reflected or scattered radiation response with a lens-based objective combined with hyperspectral spectrometer and camera system. In order to achieve a desired high measurement speed, low numerical aperture optics, with field-of-view large enough for the entire sample (up to 300 mm) may be used. Such an arrangement allows for high measurement speed, e.g., dozens of wafers per hour, and high resolution, e.g., around hundred microns per pixel. The low numerical aperture of the objective, however, may lead to a large distance between the signal-collecting optics and sample. The optical signal collection efficiency therefore may be approved upon.

One way to improve the optical signal collection efficiency, for example, is by using higher numerical aperture optics, thereby enabling a decrease in the optics-to-sample distance thereby increasing the signal collection efficiency, however, at the expense of a reduced optics field-of-view. With the use of higher numerical aperture optics, only a portion of sample is scanned or viewed in one imaging cycle. Consequently, a series of measurements and image stitching are necessary for reconstructing an image of the entire sample. Such a solution inherently leads to low measurement speed and, ultimately, low measurement throughput.

Accordingly, in another embodiment, high NA optics having a length that e.g., is equal to or exceeds the desired image size, may be used to deliver a high collection efficiency of the optical signal. With the use of a signal collecting optic that extends over a length, e.g., a third, a half or the entire length of the illumination lines, the signal collecting optic may be placed close to the sample surface. It should be understood that if the signal collection optics extends a third of the length of the illumination line, then three scans will be necessary to capture data for the entire image, and likewise, if the signal collection optics extends a half of the length of the illumination line, then two scans will be necessary to capture data for the entire image, thereby reducing throughput relative to a signal collection optics that extends over the entire length of the illumination line. For example, the distance from the signal collection optic to the sample and the width of the signal collection optic may be configured to produce signal collection half-angle θ that is sufficient to produce an NA of 0.4 or higher. The high NA signal collection optics may be reflective or refractive based. Additionally, an optical conduit may be used with the optics to provide the received light to the detector. The implementation enables high resolution and high sensitivity signal collection at full sample size FOV, which allows overcoming the existing trade-offs between the high resolution, sensitivity, and speed.

Figure 13:
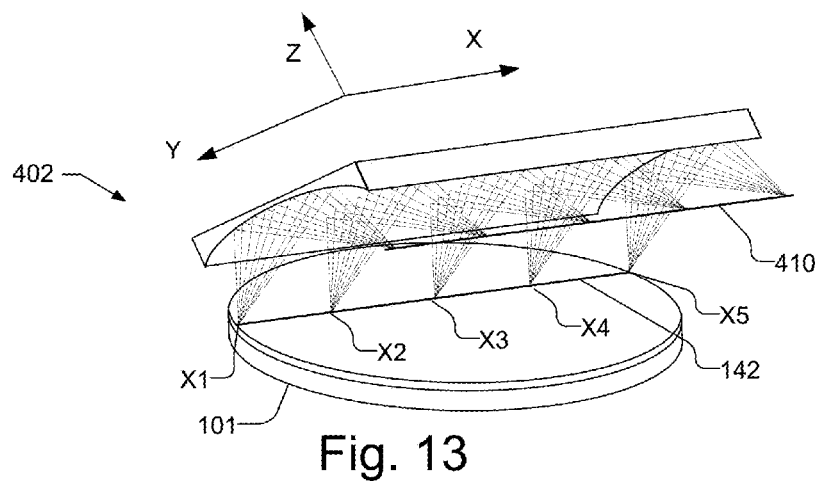
FIG. 13 illustrates a perspective view of a long elliptical cylindrical mirror that may be used to receive photoluminescence light emitted from the sample.

For example, in one embodiment, in order to collect the photoluminescence or scattered radiation across the excitation line 122 shown in FIG. 1, reflective optics may be used, such as a long elliptical cylindrical mirror, e.g., a mirror having a right-elliptic-cylinder surface. By way of example, FIG. 13 illustrates a perspective view of a long elliptical cylindrical mirror 402 that may be used to receive photoluminescence emitted from the sample 101 or light scattered the sample 101. In the length direction, along the X axis, the mirror 402 is flat, while in the width direction, along the Y axis, the mirror 402 is elliptically curved with high NA, i.e. short focal distance. For example, the distance from the mirror to the sample may be 10 mm, and the contour size of the mirror may also be 10 mm, and thus, the signal collection half-angle θ is about 26 degrees, leading to an NA=0.45. The length of mirror 402, for example, may exceed the desired image size, e.g., 300 mm sample size for the current wafer technology. The mirror 402, along with collection optics, and spectrometer, discussed below, may be used in place of the detector 130, e.g., illustrated in FIGS. 1, 3A, 4A, 7, 11, and 12.

Figure 14:
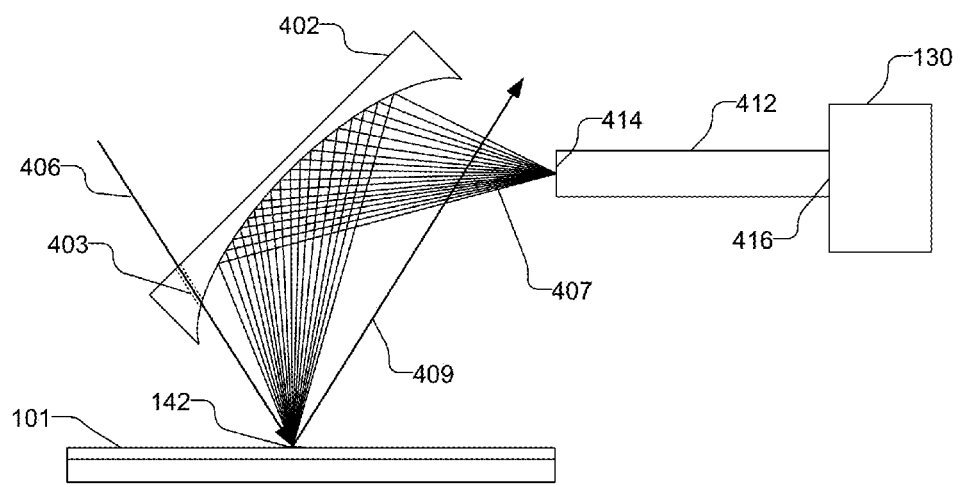
FIG. 14 illustrates a side view (along the Y-Z plane) of the elliptical mirror collecting photoluminescence or scattered radiation from the sample.

FIG. 14 illustrates a side view (along the Y-Z plane) of the elliptical mirror 402 collecting photoluminescence or scattered radiation from a sample 101. The mirror 402 may be placed in close proximity (several to a few dozen millimeters) to the sample 404 leading to a high collection efficiency of the optical photoluminescence or scattered radiation signal generated by the excitation laser beam 406. The mirror 402 may include a slit 403 or multiple slits, through which the excitation laser beam 406 may pass through. Alternatively, the excitation laser beam 406 may pass under the mirror 402, however, the use of a slit 403 permits the usage of a wider mirror, thus offering higher NA and better signal sensitivity. The laser beam 406 is scanned in the X direction across the wafer, e.g., with scanning system 116, shown in FIG. 1, or the like. At each desired spatial position (along the X direction) along line 142 (illustrated in FIG. 13 as positions X1, X2, X3, X4, and X5), the mirror 402 collects the optical signal 407 from the sample 404 at a wide angle, which leads to a high instrument sensitivity. It should be understood that while discrete positions X1, X2, X3, X4, and X5 are illustrated in FIG. 13, the beam 406 scans continuously across the sample 404, and an optical signal 407 from all positions along the line 142 is received by the mirror 402. Due to the linear configuration of the mirror 402 along the X direction, as illustrated in FIG. 13, with the excitation region being in a form of a line 142 across the entire sample in the X direction of the sample 404, the resulting optical signal 407, e.g., the photoluminescence radiation emitted from the sample 404 or radiation scattered by sample 404, is focused by the elliptical cylindrical mirror 402 into a line 410 of the same length as the excitation line 142. The excitation line 142 and line 410 may have the same length as the mirror 402, i.e., a length that exceeds the desired image size, e.g., on the order of 300 mm.

The sample 404 is excited in a form of a line generated by moving the excitation beam 406 along the sample with the scanning system 116. In one arrangement, in order to excite the sample 404, the excitation beam 406 may pass outside the mirror 402 as the excitation beam 406 is scanned along the X direction. In one arrangement, the excitation beam 406 may pass under or over the mirror 402. In another arrangement, the elliptical cylindrical mirror 402 may be include a narrow slit along the mirror length, such that the beam 406 may pass through the slit in the mirror 402 and may excite the sample 404 at any desirable angle, including normal angle.

The resulting optical signal 407 focused along the line 410, as shown in FIG. 13, is obtained via focusing photoluminescence or scattered radiation with the elliptical cylindrical mirror 402. The resulting optical signal 407, which is focused along the line 410 needs to be delivered to a detector 130 for the purpose of recording the optical signal. Detectors, however, typically do not have input apertures in the shape of a 300 mm long line. Accordingly, the resulting optical signal 407, which is focused along line 410 should be matched to the aperture of the detector 130, with a minimal loss of light. In one embodiment, the resulting optical signal 407 focused by mirror 402 may be received by an optical conduit 412, which has a linear signal reception end 414 (aligned with the line 410 in FIG. 13), and a signal output end 416 having a shape that is compatible with the aperture of detector 130. As illustrated, the specularly reflected light 409 is not received by the mirror 402 or the optical conduit 412. If desired, the mirror 402 may include a slit (not shown) through which the specularly reflected light 409 passes through.

Figure 15:
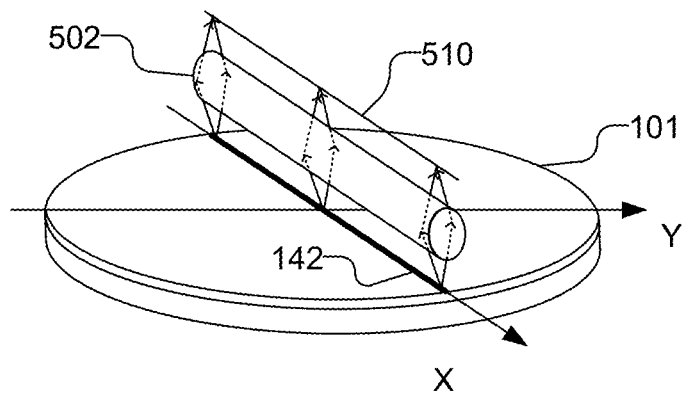
FIG. 15 illustrates a perspective view of a long cylindrical lens that may be used to receive photoluminescence emitted from the sample.

In another embodiment, in order to collect the photoluminescence or scattered radiation across the excitation line 122 shown in FIG. 1, refractive optics may be used, such as a long cylindrical focusing lens, e.g., a lens having a right-circular-cylinder shape. By way of example, FIG. 15 illustrates a perspective view of a long cylindrical lens 502 that may be used to receive photoluminescence emitted from the sample 101 or light scattered the sample 101. The cylindrical lens 502 may have a high NA, i.e. short focal distance. For example, if the diameter of the cylindrical lens is about 20 mm, and the lens center is also at distance of 20 mm from the sample, i.e. the air gap between the sample and the lens is 10 mm, leading to an NA=0.45. The length of lens 502, for example, may exceed the desired image size, e.g., 300 mm sample size for the current wafer technology. The lens 502, along with collection optics, and spectrometer, discussed below, may be used in place of the detector 130, e.g., illustrated in FIGS. 1, 3A, 4A, 7, 11, and 12.

Figure 16:
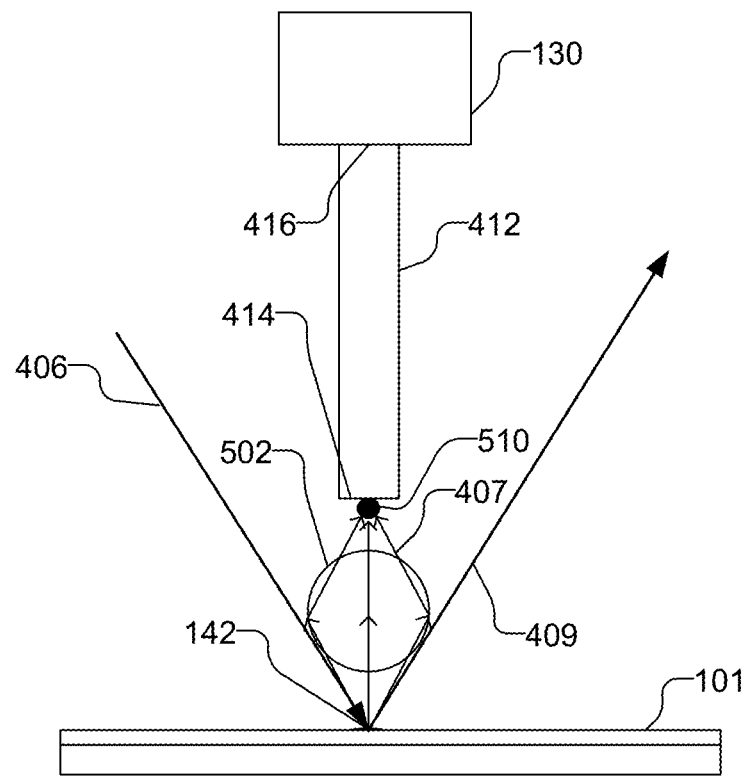
FIG. 16 illustrates a side view (along the Y-Z plane) of the cylindrical lens collecting photoluminescence or scattered radiation from the sample.

FIG. 16 illustrates a side view (along the Y-Z plane) of the cylindrical lens 502 collecting photoluminescence or scattered radiation from a sample 101. The cylindrical lens 502 may be placed in close proximity (several to a few dozen millimeters) to the sample 101 leading to a high collection efficiency of the optical photoluminescence or scattered radiation signal generated by the excitation laser beam 406. The laser beam 406 is scanned in the X direction across the wafer, e.g., with scanning system 116, shown in FIG. 1, or the like. The cylindrical lens 502 collects the optical signals 407 from the sample 101 along the length of the line 142 (shown in FIG. 15) on the sample 101 at a wide angle, which leads to a high instrument sensitivity. Due to the linear configuration of the cylindrical lens 502 along the X direction, as illustrated in FIG. 15, with the excitation region being in a form of a line 142 across the entire sample in the X direction of the sample 404, the resulting optical signal 407, e.g., the photoluminescence radiation emitted from the sample 404 or radiation scattered by sample 404, is focused by the cylindrical lens 502 into a line 510 of the same length as the excitation line 142. The excitation line 142 and line 510 may have the same length as the cylindrical lens 502, i.e., a length that exceeds the desired image size, e.g., on the order of 300 mm.

The sample 101 is excited in a form of a line generated by moving the excitation beam 406 along the sample with the scanning system 116. As illustrated, to excite the sample 101, the excitation beam 406 passes below the cylindrical lens 502 as the excitation beam 406 is scanned along the X direction. The resulting optical signal 407 focused along the line 510, as shown in FIG. 15, is obtained via focusing photoluminescence or scattered radiation with the cylindrical lens 502. The resulting optical signal 407, which is focused along the line 510 needs to be delivered to a detector 130 for the purpose of recording the optical signal. As discussed above, the resulting optical signal 407, which is focused along line 510 should be matched to the aperture of the detector 130, with a minimal loss of light. In one embodiment, the resulting optical signal 407 focused by cylindrical lens 502 may be received by an optical conduit 412, which has a linear signal reception end 414 (aligned with the line 510 in FIG. 15), and a signal output end 416 having a shape that is compatible with the aperture of detector 130. As illustrated, the specularly reflected light 409 is not received by the cylindrical lens 502 or the optical conduit 412.

Figure 17A:
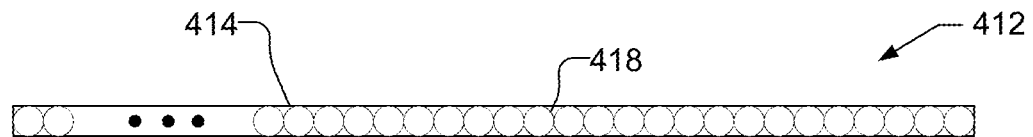
FIGS. 17A and 17B illustrate the reception end and output end, respectively, of an optical conduit of numerous optical fibers.
Figure 17B:
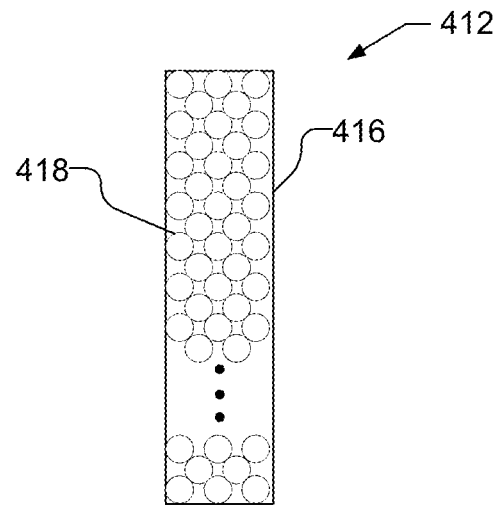

FIG. 17A illustrates the linear signal reception end 414 of the optical conduit 412 to receive the optical signal 407 from the optics 402 or 502 and FIG. 17B illustrates a rectangular signal output end 416 to provide the optical signal 407 to the detector 130. The optical conduit 412 includes numerous optical fibers 418 between the linear signal reception end 414 and a rectangular signal output end 416. As illustrated, the fibers 418 may be arranged at the linear signal reception end 414 in a single row that matches the length of the optical signal 407 or to match the length of the optics, e.g., elliptical cylindrical mirror 402 or cylindrical lens 502. By way of example, 1298 fibers can be used, each of 0.245 mm in diameter to form a line which is approximately 318 mm long, slightly larger than the 300 mm sample in order to collect most of signals from the sample edges. If desired, a different number of fibers or different fiber diameters may be used, or a different number of fiber rows may be used at the linear signal reception end 414. Moreover, if the sample size is different, e.g., 200 mm, a different number of fibers may be used, e.g., 891 fibers can be used to form a line which is approximately 218 mm long. Of course, if the length of the optical conduit 412 is shorter than the length of the optics 402 or 502, a portion of the optical signal 407 may not be received by the optical conduit 412, and thus, the detector 130, and multiple passes may be required to acquire data for the entire sample. The fibers 418 are mechanically re-arranged from the linear signal reception end 414 to the rectangular signal output end 416. For example, as illustrated in FIG. 17B, the fibers may be arranged in a number of layers. For example, 1298 fibers on the linear signal reception end 414 may be re-arranged into 118 layers by 11 layers giving the same number of fibers on the spectrometer side (118×11=1298 fibers). For a different sized sample, e.g., a 200 mm sample, where 891 fibers are on the linear signal reception end 414, the 891 fibers may be re-arranged into 81 layers by 11 layers giving the same number of fibers on the spectrometer side (81×11=891 fibers). The re-arrangement into the rectangular shape of 81 by 11 layers, per the example, resizes the optical conduit 412 from 218 mm long (by 0.245 mm) at the linear signal reception end 414 to approximately 20 mm by 2.5 mm at the rectangular signal output end 416, which is accepted by the detector 130. Thus, the optical signal 407 is focused by the optics 402 or 502 into the linear signal reception end 414 and the optical fibers 418 are used to provide the optical signal to the rectangular signal output end 416, which is coupled to the detector 130. Such arrangement facilitates delivery of the optical signal 407 into the signal detector 130, which ultimately converts the optical radiation into electrical signal. Different shapes on the signal output end 416 of the optical conduit 412 can be used such as, for example, rectangular, square or circular. Additionally, further focusing optics may be applied between the rectangular signal output end 416 and the detector 130 to achieve even better matching, if desirable.

Figure 18:
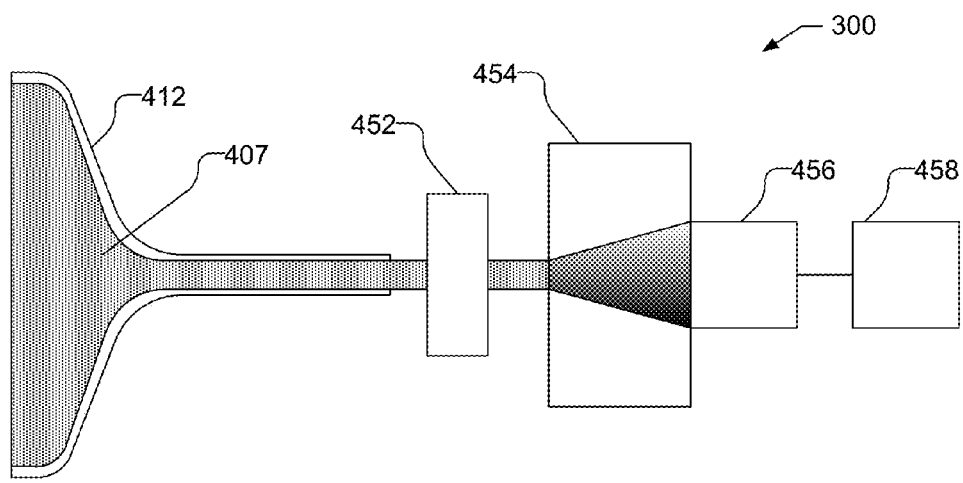
FIG. 18 illustrates an optical conduit providing collected light to a detector that includes a spectrometer.

The optical signal 407 upon exiting from the optical conduit 412 may by further formed by the exit optics to match the signal to the detector input. A variety of the detection scenarios can be used depending on the desired end result. For example, the detector 130 may use a spectrometer. As illustrated in FIG. 18, the optical signal 407 after exiting the optical conduit 412 may be filtered by an optical filter 452 and provided to the slit of a spectrometer 454, where the light is dispersed by a grating or prism into different wavelengths, and finally delivered into the array of CCD or CMOS camera sensors 456 and recorded by a data acquisition device 458, which provides the data to the processor 152 for analysis. Thus, the detector 130 may capture multiple output signals while the excitation beam 406 is scanned across the wafer in the X direction in order to obtain spectral and spatial information.

Figure 19:
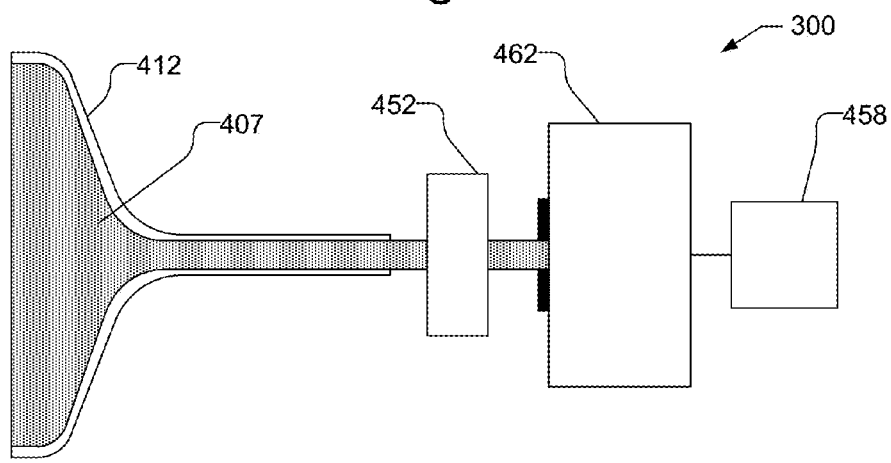
FIG. 19 illustrates an optical conduit providing collected light to a detector that includes a Photomultiplier Tube (PMT) or Avalanche Photo Diode (APD).

In another embodiment, the detector 130 may use a Photo Multiplier Tube (PMT) or avalanche photodiode (APD). As illustrated in FIG. 19, the optical signal 407 after exiting the optical conduit 412 may be filtered by an optical filter 452 and provided to the Photomultiplier Tube (PMT) or Avalanche Photo Diode (APD) 462. The optical signal 407 is converted into electrical signal and is recorded by the data acquisition device 458, which provides the data to the processor 152 for analysis. In this embodiment, no spectral information is acquired, but rather all wavelengths are integrated into one electrical signal. Thus, it may be desirable to synchronize the first light source 110 and the second light source 140 (FIG. 1) so that the resulting signals are not received at the same time by the detector 130.

Figure 20:
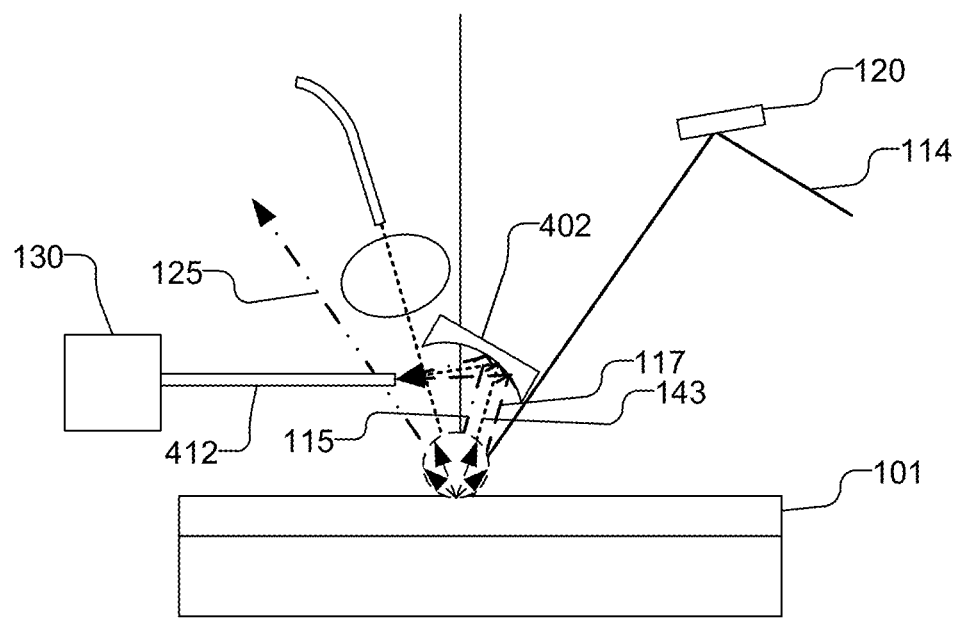
FIG. 20 illustrates a side view (along the Y-Z plane) of the simultaneous collection of dark field scattered radiation, photoluminescence light, and optionally, bright field reflectance radiation by an optical metrology device employing an elliptical mirror.

FIG. 20 illustrates a side view (along the Y-Z plane) illustrating, by way of example, the simultaneous collection of dark field scattered radiation, photoluminescence light, and optionally, bright field reflectance radiation, by the optical metrology device using the elliptical mirror 402 with the optical conduit 412. As illustrated, the illumination beam 114 generates scattered light 115, and excites photoluminescence light 117, that are received by the spectrometer 134, along with the reflected broadband light 143.

The detector 130, which may include including optics 132, spectrometer 134, and sensor 136 can simultaneously record the photoluminescence light generated in the sample 101 in response to excitation by the illumination beam 114 and scattered light from the illumination beam 114, and optionally a bright field reflection of the broadband light 143, e.g., if the optical conduit 412 has a signal output end in the form of a line to provide spatial information. If desired, the detector 130 may further record a dark field scattering of the illumination beam 114 by defects on the sample so that, if desired, three separate signals are simultaneously imaged. The detector 130 is used to collect all three signals, so that there is no spatial or time shifts between the three signals. A spectrometer 134 separates the signals into three different spectral information channels, i.e., signals are spectrally separated that are recorded in different wavelength bins (sensor pixels) with the 2D sensor array sensor of the detector 130.

With the use of the elliptical mirror 402, the optical signal emitted from the surface of the sample 101 is collected by high NA mirror-based optics, which delivers high collection efficiency of the optical signal and high instrument sensitivity. In the X direction, the sample is excited in a form of a line generated by scanning system 116, which enables high measurement speed. The measurement arrangement is complemented by application of an optical conduit 412, which enables collection of the optical signal from a sample-size-long line and transformation of the optical signal into a desired shape without any mechanical movement, such as a small circular area or in a line. Application of the multi-fiber conduit with several thousand individual fibers enables high measurement resolutions on the order of tens of microns per pixel. As a result, the apparatus delivers high sensitivity, high resolution and high speed (measurement throughput).

Although specific embodiments are provided herein for instructional purposes, the described embodiments are not limiting. Various adaptations and modifications may be made without departing from the scope of the present discloser. For example, a rotary stage may be used in place of a linear stage for scanning the illumination lines 122 and 142 across the surface of the sample 101. Moreover, the scanning system 116 may be modified to eliminate, e.g., the fixed mirror, or an F-theta lens may be used for focusing the illumination beam 114 on the surface of the sample 101. Other modifications and variations are possible, and therefore, the spirit and scope of the appended claims should not be limited to the foregoing description.

What is claimed is:

1. An apparatus comprising:
    an illumination source that produces a first light beam;
    a first lens system that causes the first light beam to be incident on a surface of a sample as a first illumination line orientated along a first direction, the first illumination line being incident on the sample at a first angle of incidence, wherein the sample emits photoluminescence light in response to excitation caused by the first light beam along the first illumination line;
    a second illumination source;
    a second lens system that focuses light emitted by the second illumination source onto the sample as a second illumination line orientated along the first direction and that is overlaid on the first illumination line on the surface of the sample and that is incident on the sample at a second angle of incidence that is different than the first angle of incidence;
    a stage for providing relative movement between the sample and first and second illumination lines in a second direction that is different than the first direction;

a detector that collects reflected light from the second illumination line and receives the photoluminescence light emitted by the sample along the first illumination line; and a processor coupled to the detector and configured to determine a characteristic of the sample for a plurality of positions on the surface of the sample using the photoluminescence light and the reflected light.

2. The apparatus of claim 1, further comprising:

a signal collecting optic extending a length of the first and second illumination lines, the signal collecting optic receives the photoluminescence light from the first illumination line and the reflected light from the second illumination line and focuses the photoluminescence light and the reflected light into a line; and an optical conduit having a linear reception end that receives the photoluminescence light and the reflected light focused by the signal collecting optic, the optical conduit further having an output end that is configured to provide the photoluminescence light and the reflected light to the detector, the output end having a different shape than the linear reception end.

3. The apparatus of claim 2, wherein the signal collecting optic is one of an elliptical cylindrical mirror or a cylindrical lens.

4. The apparatus of claim 3, wherein the signal collecting optic has a numerical aperture (NA) of 0.4 or greater.

5. The apparatus of claim 2, wherein the optical conduit comprises a plurality of optical fibers, the optical fibers have a first arrangement at the linear reception end and a second arrangement that is different than the first arrangement at the output end, and wherein the output end has a shape that matches a shape of an entrance aperture of the detector.

6. The apparatus of claim 1, wherein a portion of the first light beam is scattered off surface defects on the sample producing scatter signals along the first illumination line, the detector receives the scatter signals.

7. The apparatus of claim 6, wherein the processor generates a surface defect image of the sample using the scatter signals received from the detector.

8. The apparatus of claim 1, wherein the first lens system comprises a scanning mirror to scan the first light across the sample in the first direction to form the first illumination line.

9. The apparatus of claim 1, wherein the first illumination line and the second illumination line are produced concurrently.

10. The apparatus of claim 1, wherein the first illumination line and the second illumination line are produced sequentially.

11. The apparatus of claim 1, wherein the detector comprises a Photomultiplier Tube (PMT) or Avalanche Photo Diode (APD).

12. The apparatus of claim 1, wherein the second illumination source is a broadband light source that produces broadband light and the reflected light is reflected broadband light, and wherein the detector images the reflected broadband light and the photoluminescence light on a two-dimensional array with a first dimension representing spatial information along the first direction and a second dimension representing spectral information of the reflected broadband light and the photoluminescence light and produces an image frame in response, wherein the detector produces a plurality of image frames for a plurality of positions of the first illumination line and the second illumination line that are overlaid on the surface of the sample as the stage moves the sample in the second direction.

13. An apparatus comprising:

a light source that produces an illumination beam;

an optical system that receives the illumination beam and produces an illumination spot on a surface of a sample;

a scanning system that scans the illumination spot to form an illumination line across the sample, wherein the sample emits photoluminescence light in response to excitation caused by the illumination spot along the illumination line;

a stage for providing relative movement between the illumination line and the sample;

a signal collecting optic extending a length of the illumination line, the signal collecting optic receives the photoluminescence light from the illumination line and focuses the photoluminescence light into a line;

an optical conduit having a linear reception end that receives the photoluminescence light focused by the signal collecting optic, the optical conduit further having an output end having a different shape than the linear reception end;

a detector that collects the photoluminescence light from the optical conduit, the detector having an entrance aperture that matches a shape of the output end of the optical conduit; and a processor coupled to the detector to receive the photoluminescence light to determine a characteristic of the sample.

14. The apparatus of claim 13, wherein the signal collecting optic is one of an elliptical cylindrical mirror or a cylindrical lens.

15. The apparatus of claim 14, wherein the signal collecting optic has a numerical aperture (NA) of 0.4 or greater.

16. The apparatus of claim 13, wherein the optical conduit comprises a plurality of optical fibers, the optical fibers have a first arrangement at the linear reception end and a second arrangement that is different than the first arrangement at the output end.

17. The apparatus of claim 13, wherein a portion of the illumination beam is scattered off surface defects on the sample producing scatter signals along the illumination line, wherein the signal collecting optic receives the scatter signals and the scatter signals are provided to the detector with the optical conduit.

18. The apparatus of claim 13, wherein the scanning system scans the illumination beam in a plane that is at a non-normal angle of incidence on the sample.

19. The apparatus of claim 13, wherein the detector comprises a Photomultiplier Tube (PMT) or Avalanche Photo Diode (APD).

20. The apparatus of claim 13, wherein all wavelengths in the illumination beam are simultaneously combined in the illumination spot, and wherein the detector images the photoluminescence light emitted along the illumination line on a two-dimensional array with a first dimension representing spatial information along the illumination line and a second dimension represent spectral information of the photoluminescence light, wherein the detector produces an image frame representing the photoluminescence light emitted along the illumination line, and wherein the detector produces a plurality of image frames for the illumination line on the surface of the sample as the stage produces relative movement between the illumination line and the sample.

21. The apparatus of claim 13, wherein the illumination beam is a first illumination beam, the illumination line is a first illumination line, the apparatus further comprising:

a broadband light source that produces broadband light; and a lens that focuses the broadband light into a second illumination line on the surface of the sample, the second illumination line overlays and is aligned with the first illumination line and is incident on the sample at an angle of incidence that is different than an angle of incidence of a plane of the illumination beam, wherein the second illumination line is reflected by the sample to produce reflected light;

wherein the signal collecting optic further receives the reflected light and focuses the reflected light into the line and the optical conduit receives the reflected light from the signal collecting optic; and wherein the detector collects the reflected light from the optical conduit, and wherein the processor further determines the characteristic of the sample using the reflected light.

22. The apparatus of claim 21, wherein the signal collecting optic receives specularly reflected broadband light.

23. The apparatus of claim 13, wherein the scanning system that scans the illumination spot to form the illumination line on the surface of the sample comprises a galvanometric mirror or a polygonal mirror.

24. A method comprising:
illuminating a surface of a sample with a light source along an illumination line having an orientation in a first direction, wherein the sample emits photoluminescence light from the illumination line in response to excitation caused by light from the light source;

collecting the photoluminescence light from the illumination line with a signal collecting optic along a length of the illumination line and focusing the photoluminescence light into a line with the signal collection optic;

receiving the photoluminescence light along the line with an optical conduit having a linear reception end and outputting the photoluminescence light from the optical conduit at an output end having a different shape than the linear reception end;

detecting the photoluminescence light received from the output end of the optical conduit with a detector having an entrance aperture that matches a shape of the output end of the optical conduit;

moving the illumination line across the surface of the sample in a second direction that is different than the first direction; and determining a characteristic of the sample for a plurality of positions on the surface of the sample using the photoluminescence light detected by the detector.

25. The method of claim 24, wherein the signal collecting optic is one of an elliptical cylindrical mirror or a cylindrical lens and has a numerical aperture (NA) of 0.4 or greater.

26. The method of claim 24, further comprising transmitting the photoluminescence light with a plurality of optical fibers in the optical conduit, wherein the optical fibers have a first arrangement at the linear reception end and a second arrangement that is different than the first arrangement at the output end.

27. The method of claim 24, wherein a portion of the illumination is scattered off surface defects on the sample producing scatter signals along the illumination line, the method further comprising collecting the scatter signals with the signal collecting optic and providing the scatter signals to the detector with the optical conduit.

28. The method of claim 24, wherein the detecting the photoluminescence light is performed by one of a Photomultiplier Tube (PMT), Avalanche Photo Diode (APD), or a spectrometer.

* * * * *